US005610031A

United States Patent [19]
Burgeson et al.

[11] Patent Number: 5,610,031
[45] Date of Patent: Mar. 11, 1997

[54] B1K CHAIN OF LAMININ AND METHODS OF USE

[75] Inventors: Robert E. Burgeson, Marblehead; David W. Wagman, Melrose, both of Mass.

[73] Assignees: The General Hospital Corporation, Boston, Mass.; The State of Oregon Acting By & Thru the State Board .. ., Portland, Oreg.

[21] Appl. No.: 144,121

[22] Filed: Oct. 27, 1993

[51] Int. Cl.⁶ .......................... C12N 15/11; C12N 15/12; C07K 14/78
[52] U.S. Cl. ................. 435/69.1; 435/252.3; 435/172.3; 435/320.1; 435/325; 435/354; 536/23.1; 536/23.5; 530/350; 530/353; 530/395
[58] Field of Search ................................ 536/23.5, 23.1; 435/69.1, 252.3, 240.2, 172.3, 320.1; 530/350, 353, 395

[56] References Cited

U.S. PATENT DOCUMENTS 5,003,044  3/1991  Hunter et al. ........................... 530/326

FOREIGN PATENT DOCUMENTS

WO92/17498  10/1992  WIPO .

OTHER PUBLICATIONS

D. Gerecke et al. "cDNAs Encoding for Two of the Chains of the . . . " Matrix 13(1) 20–21 (Jan 1993).
S. L. Berger et al. (eds.) "Guide to Molecular Cloning Techniques" Meth. in Enzymology vol. 152 pp. 316–337, 343–349, 359–371, 451–469, 661–704.
U.S. application Ser. No. 08/141,233, filed Oct., 1993, Burgeson et al.
Aratani et al., "Enhanced Synthesis and Secretion of Type IV Collagen and Entactin during Adipose Conversion of 3T3–L1 Cells and Production of Unorthodox Laminin Complex" *The Journal of Biological Chemistry*, vol. 263, No. 31, pp. 16163–16169, (1988).
Beck et al., "Structure and Function of Laminin: Anatomy of a Multidomain Glycoprotein" *The FASEB Journal*, vol. 4, pp. 148–160, (1990).
Cooper et al., "Studies on the Biosynthesis of Laminin by Murine Parietal Endoderm Cells" *European Journal of Biochemistry*, vol. 119, pp. 189–197, (1981).
Davis et al., "Isolation and Characterization of Rat Schwannoma Neurite–promoting Factor: Evidence that the Factor Contains Laminin" *The Journal of Neuroscience*, vol. 5, No. 10, pp. 2662–2671, (1985).
Edgar et al., "Structural Requirements for the Stimulation of Neurite Outgrowth by Two Variants of Laminin and Their Inhibition by Antibodies" *The Journal of Cell Biology*, vol. 106, pp. 1299–1306, (1988).
Ehrig et al., "Merosin, A Tissue–Specific Basement Membrane Protein, is a Laminin–Like Protein" *Proceedings of the National Academy of Sciences*, vol. 87, pp. 3264–3268, (1990).

Engvall et al., "Distribution and Isolation of Four Laminin Variants; Tissue Restricted Distribution of Heterotrimers Assembled From Five Different Subunits" *Cell Regulation*, vol. 1, pp. 731–740, (1990).
Engvall et al., "Mapping of Domains in Human Laminin Using Monoclonal Antibodies: Localization of the Neurite–Promoting Site" *The Journal of Cell Biology*, vol. 103, No. 6, pp. 2457–2465, (1986).
Frenette et al., "Biosynthesis and Secretion of Laminin and Laminin–associated Glycoproteins by Nonmalignant and Malignant Human Keratinocytes: Comparison of Cell Lines from Primary and Secondary Tumors in the Same Patient" *Cancer Res*, vol. 48, pp. 5193–5202, (1988).
Gerecke et al., "cDNA's Encoding for the Three Chains of the Anchoring Filament Protein Kalinin Show Similarity to the Laminin A B1 and B2 Chains", *Mol. Biol. Cell*, vol. 3, (suppl.), p. #1A, (1992).
Hunter et al., "Laminin Chain Assembly by Triple and Double Stranded Coiled–Coil Structures", *The Journal of Biological Chemistry*, vol. 267, No. 9 pp. 6006–6011, (1992).
Hunter et al., "Expression of S–Laminin and Laminin in the Developing Rat Central Nervous System" *The Journal of Comparative Neurology*, vol. 323, pp. 238–251, (1992).
Hunter et al., "An LRE (Leucine–Arginine–Glutamate)–dependent Mechanism for Adhesion of Neurons to S–laminin" *The Journal of Neuroscience*, vol. 11, No. 12, pp. 3960–3671, (1991).
Hunter et al., "Primary Sequence of a Motor Neuron–Selective Adhesive Site in the Synaptic Basal Lamina Protein S–Laminin" *Cell*, vol. 59, pp. 905–913, (1989).
Liesi et al., "Glial Cells of Mammalian Brain Produce a Variant Form of Laminin" *Experimental Neurology*, vol. 105, pp. 86–92, 1989.
Marinkovich et al., "The Anchoring Filament Protein Kalinin Is Synthesized and Secreted as a High Molecular Weight Precursor", *The Journal of Biological Chemistry*, vol. 267, No. 25, pp. 17900–17906, (1992).
Marinkovich et al., "The Dermal–Epidermal Junction of Human Skin Contains a Novel Laminin Variant" *The Journal of Cell Biology*, vol. 119, No. 3, pp. 695–703, 1992.
Marinkovich et al., "Characterization of a Novel Laminin Isoform Produced by Human Keratinocytes In Vitro", *Clinical Research*, vol. 39, No. 2, pp. #565A, (1991).
Morita et al., "Post–translational Assembly and Glycosylation of Laminin Subunits in Parietal Endoderm–like F9 Cells" *Biochemistry Journal*, vol. 229, pp. 259–264, (1985).
Paulsson et al., "Mouse Heart Laminin" *The Journal of Biological Chemistry*, vol. 264, No. 31, pp. 18726–18732, 1989.

(List continued on next page.)

*Primary Examiner*—Charles L. Patterson, Jr.
*Assistant Examiner*—Rebecca Prouty
*Attorney, Agent, or Firm*—Louis Myers, Ph.D., Lamive & Cockfield

[57] ABSTRACT

Recombinant laminin B1k and fragments thereof.

9 Claims, 13 Drawing Sheets

OTHER PUBLICATIONS

Peters et al., "The Biosynthesis, Processing, and Secretion of Laminin by Human Choriocarcinoma Cells" *The Journal of Biological Chemistry*, vol. 260, No. 27, pp. 14732–14742, (1985).

Rouselle et al., "Kalinin: An Epithelium–Specific Basement Membrane Adhesion Molecule That Is a Component of Anchoring Filaments" *Journal Cell Biology*, vol. 114, pp. 567–576, (1991).

Sanes et al., "S–Laminin" *Cold Spring Harbor Symposia on Quantitative Biology*, vol. 55, pp. 419–430, (1990).

Wewer et al., "Human Laminin Isolated in a Nearly Intact, Biologically Active Form from Placenta by Limited Proteolysis" *The Journal of Biological Chemistry*, vol. 258, No. 20, pp. 12654–12660, (1983).

Woodley et al., "Laminin Inhibits Human Keratinocyte Migration" *Journal of Cellular Physiology*, vol. 136, pp. 140–146, (1988).

DOMAIN VI

```
Blk    1                   QQACSRGACYPPVGDLLVGRTRFLRASSTCGLTKPETYC  TQYGEWQMKCCKCDSRQPH      NYYSHRVE
                           :|  | ||| ||||:||   |    |||||  ||| ||      : :| :|            | || :|
Ble    1  QEPEFSYGCAEGSCYPATGDLLIGRAQKLSVTSTCGLHKPEPYCIVSHLQE  DKKCFICNSQDPYHETLNPDSHLIE

Blk   67  NVASSSGPMR     WWQSQNDVNPVSLQLDLDRRFQLQEVMMEFPGAHAAGMLIERSSDFGKTWRVYQYLAADCTSTF
          ||   ||        ||||:|:|: |  ||||  |::|    ::|  | ::||||||||||||| || |:|:  |  |
Ble   77  NVVTTFAPNRLKIWQSENGVENVTIQLDIEAEFHFTHLIMTFKTFRPAAMLIERSSDFGKTWGVYRYFAYDCEASF

Blk  141  PRVRQGRPQSWQDVRCQSLPQRPNARLNGGKVQLNLMDLVSGIPATQSQKIQEVGEITNLRVNFTRLAPV      P
          | :    |  |     :|: ||:       ::  :|    |||     |||: : :||||  | :|  |      |
Ble  154  PGISTGPMKKVDDIICDS RYSDIEPSTEGEVIFRALDPAFKIEDPYSPRIQNLLKITNLRIKFVKLHTLGDNLLDS

Blk  212  KLDHPPSAYYAVSQLRLQGS
          :::            ||||   |
Ble  230  RMEIREKYYYAVYDMVVRGN
```

FIG. 3A

DOMAIN III / V

```
B1k  288  GQDAHECQRCDCNGHSENCHFDPAVFAASQGAYGGVCDNCRDHTEGKNCERCQLHYFRNRRPGASIQETCISCECDP
              | : * :|:||:||   |||| ||:   |||:  *|:|||  |||*:  * :   ||
B1e  305  GRNSNACKKCNCNEHSISCHFDMAVYLATGNVSGGVCDDCQHNTMGRNCEQCKPFYYQHPERDIRDPNFCERCTCDP

B1k  365  DGQWAGAPCDP          VTGQCVCKEHVQGERCDLCKPGFTGLTYANPQGCHR
              |  ::  ||          : |||  ||: ||:||:|| ||   *|   :| |||
B1e  382  AGSQNEGIC

DOMAIN II

```
Blk   423  PCDEESGRCLCLPNVGGPKCDQCAPYHWKLASGQGCEPCACDPHNSLSPQCNQFTGQCPCREGFGGLMCS     CDCNILPSRRL
                || - ||||||||  - ||||  ::|  ||||  ||:||  |:: :|::| ||:|||||  |||         ||| -|
Ble  1017  HCNGSDCQCDKATGQCLCLPNVIGQNCDRCAPNTWQLASGTGCDPCNCNAAHSFGPSCNEFTGQCQCMPGFGGRTCS  -569 res- CVCNYLGTVQE Blk   493  AAAIRQCPDRTYGDVATGCRACDCDFRGTEGPGCDKASG VLCRPGLTGPRCDQCQRGYCNRYPVCVA CHPCFQTY
           :|: :|| :|||||||||||| | || - ||      :|   ||  :  |||||  |||| |  :|:  ||  ||   :
Ble  1094  ECQELFWGDPDVECRACDCDPRGIETPQCDQSTGQCVCVEGVEGPRCDKCTRGYSGVFPDCTP CHQCFALW Blk   568  DADLREQALRFGRLPNATASLWSGPGLEDRGLASRILDAKSKIEQIRAVL  SSPAVTEQEVAQVASAILSRRTLQ
           |- : |||  - |- |:  |  -      |:|  | : |||||      |::::   |   :|:|::   |
Ble  1165  DVIIAELTNRTHRFLEKAKALKISGVIG  PYRETVDSVERKVSEIKDILAQSPAAEPLKNIGNLFEEAERLIKDVT Blk   643  GL QLDIPLEEET   LSLPRDLESLDRSFNGLLITMYQRKREQFEKISSADPSGAFRMLSTAYEQSAQAQQVS
           :: |:::|-|  |::|:|||:  :|  |   |:  -  ||   :|   :  : :|
Ble  1240  EMMAQVEVKLSDTTSQSNSTAKELDSLQTEAESLDNTVKELAEQLEFIKNSDIRGALDSITKYFQMSLEAEERVNAS Blk   713  DSSRLLDQLRDSRREAERLIVRQAGGGGTGSPKLVA  LRLEMSSLPDLTPTFNKL
           :| : |||:  ::  |  :   |  |:: |     :  |  |   |:::| :::|
Ble  1317  TTEPNSTVEQSALMRDRVEDVMMERESQFKEKQEEQARLLDELAGKLQSLDLSAAAEMT
```

FIG. 3C

```
                                                                              CGNSRQMACTP
                                                                                  | |
                                                                              CGTPPGASCSE
DOMAIN I

ALPHA DOMAIN

Blk  778  ISCPGELCPQDNG    TACASRC RGVLPRAGGAFLMAGQVAEQLRASMPAPA  TRQMIRAAEESASQIQSSAQRLET
               |  |   :|        |||  |::  | |: ::: ::           |:    ||  :    ||
Ble 1387  TECGGPNCRTDEGERKCGGPGC GGLVTVAHNAWQKAMDLDQDVLSALAEVEQLSKMVSEAKLRADEAKQSAEDILL

Blk  851  QVSASRSQMEEDVRRTRLLIQQVRDFLTDPDTDAATIQEVRRAVLALWLPTDSATVLQKMNEIQAIAARLPNVDLVL
          |  :      |::    |||  ||:|||||:   :     :   |    |  ::    |    :::|
Ble 1463  KTNATKEKMDKSNEELRNLIKQIRNFLTQDSADLDSIEAVANEVLKMEMPSTPQQLQNLTEDIRERVESLSQVEVIL

Blk  928  SQTKQDIGGARRLQAEAEEARSRAHAVEGQVEDVVGNLRQ        GTVALQEAQDTMQGTSRSLRLLIQDRVAEVQ
            :       |:    |    | :    |           :|  ||   : ::: :||    | :  :  :
Ble 1540  QHSAADIARAEMLLEEAKRASKSATDVKVTADMVKEALEEAEKAQVAAEKAIKQADEDIQGTQNLLTSIESETAASE

Blk  998  QVLGQQKLVTSMTKQLGDFWTRMEELRHQARQQGAEAVQAQQLAEGASEQALSAQEGFE  RIKQKYAELKDRLGQSS
            ::                :::     ||: ::|| :.:||              ::  ||  :||    ::
Ble 1617  ETL      FNASQRISELERNVEELKRKAAQNSGEAEYIERVVYTVKQSAEDVKKTLDGELDEKYKKVENLIAKKT (SEQ.I.D.NO.3)

Blk 1074  MLGEQGAR  IQSVKTEAEELFGETMEMMDRMKDMELELLRAAGH  HAALSDLTGLEKRVEQIRDHINGRVLYYSTCK
           : ::   |       |||  :::        ::|   |:|      | | |||     ||    |||||
Ble 1688  EESADARRKAEMLQNEAKTLLAQANSKLQLLKDLERKYEDNQRYLEDKAQELARLEGEVRSLLKDISQKVAVYSTCL (SEQ.I.D.NO.4)
```

FIG. 3D

| | DOMAINS (IN AMINO ACID RESIDUES) | | | | | | | |
|---|---|---|---|---|---|---|---|---|
| | VI | V | IV | III | II | α | I | TOTAL |
| LAMINEN B1e | 249 | 278 | 227 | 404 | 218 | 33 | 356 | 1765 |
| LAMINEN B1k | 231 | 180 | 0 | 148 | 207 | 31 | 351 | 1148 |

| | VI | V | IV | III | II | α | I | TOTAL |
|---|---|---|---|---|---|---|---|---|
| PERCENT AMINO ACID RESIDUE IDENTITY | 41.1 | 46.1 | - | 51.4 | 20.3 | 29.0 | 21.7 | 34.1 |

FIG. 5

```
                                                                                    ↓
Blk    1     QQA*SR*A*PV***TRF*RAS****T*T****TQYG*WQMCK**RQ
Ble^   1     QEPEFSYGCAEGSCYPATGDLLIGRAQKLSVTSTCGLHKPEPYCIVSHLQE DKKCFICNSQD
Bls>   1     QVPSLDVPSR******V*DR*TAS******S*Q*******D E**L*D*RR

Blk   57     *H      *YYRV*ASSSG*M*       ****Q*D*NP*SL****DRR*OLOEVM*E*PGAHA*G
Ble   64     PYHETLNPDSHLIENVVTTFAPNRLKIWWQSENGVENVTIQLDLEAEFHFTHLIMTFKTFRPAA
Bls   65     *FSARD*NRIQ**S*Q*RTA******PM********************

Blk  114     *********RQ*L*ATSTRVRQ*RPQSWQ*VR*Q*LPORPNARLNG*K*OLNLM
Ble  128     MLIERSSDFGKTWGVYRYFAYDCEASFPGISTGPMKKVDDIICDS RYSDIEPSTEGEVIFRAL
Bls  129     *V**ARR****S*G*D****PLA*PRRW**VV*E**********Y*V*

Blk  178     *LVSG**ATO*OKEVGE********APV     PKLDHPPSA**SOLRLO*S* (SEQ.ID.NO.5)
Ble  191     DPAFKIEDPYSPRIQNLLKITNLRIKFVKLHTLGDNLLDSRMEIREKYYYAVYDMVVRGN (SEQ.ID.NO.6)
Bls  192     ***IP*P****S***********VNLTR*********P*R*******L*EL*I** (SEQ.ID.NO.7)
```

^PIKKARAINEN et al, 1987
>HUNTER et al, 1989

```
RAT    LAMBIS*  RES.#1637  EALKLKRAGNSLAASTAEETAGSAQSRAREAEKQLREQVG (SEQ.I.D.NO.8)
                                     |||||||||||||||||||||        |||
HUMAN  LAMBIS   PEPTIDE              AGNSLAASTAEETAGSAQGRAQEA (SEQ.I.D.NO.9)

HUMAN  LAMBIK   RES.#1021  EELRHQARQGAEAVQAQQLAEGASEQALSAQEGFERIKQ (SEQ.I.D.NO.10)

HUMAN  LAMB2T^  RES.#428   TGDCYSGDENPDIECADCPIGFYNDPHDPRSCKPCPCHNG (SEQ.I.D.NO.11)
                                     ||||||||||||||||||
HUMAN  LAMB2T   PEPTIDE              DENPDIECADCPIGFYN (SEQ.I.D.NO.12)

HUMAN  LAMB2T^  RES.#1083  KVDTRAKNAGVTIQDTLNTLDGLLHLMDQPLSVDEEGLVL (SEQ.I.D.NO.13)
                                  |||||||||||||||||||||||||||
HUMAN  LAMB2T   PEPTIDE           NAGVTIQDTLNTLDGLLHLMDQPLS (SEQ.I.D.NO.14)
```

*HUNTER ET AL, 1989
^KALLUNKI ET AL, 1992

FIG. 6

|  | PERCENT IDENTITY | PERCENT SIMILARITY |
|---|---|---|
| HUMAN LAMININ B1e | 34.1 | 53.6 |
| HUMAN LAMININ B2e | 28.4 | 49.6 |
| HUMAN LAMININ B2t | 21.4 | 43.1 |
| RAT LAMININ B1s | 37.1 | 56.2 |

B1K CHAIN OF LAMININ AND METHODS OF USE

This invention was made with government support. The U.S. government may have certain rights in this invention.

BACKGROUND OF THE INVENTION

The present invention relates to adhesion proteins and to methods of using them, e.g., to promote the adhesion of cells to a substrate, e.g., to human dermis. In particular, overlapping cDNA clones encoding the entire laminin B1k chain and recombinant proteins expressed therefrom are disclosed.

The structure of the prototype laminin, a glycoprotein component of most, if not all, basement membranes has been well described in a number of species. Its overall appearance, as visualized by rotary shawdowing, is cross-shaped with a single long arm arising from the coiled-coil interaction of three separate polypeptide chains and three short arms, each originating from the individual polypeptide chains. The three chains are: A, typified by the Ae chain of EHS laminin (400-kD); B1, typified by the B1e chain of EHS laminin (220-kD); and B2, typified by the B2e chain of EHS laminin (210-kD) chains. The primary structure for each of the three prototypic polypeptide chains in humans has been elucidated by overlapping cDNAs.

Additional polypeptides that are related to the laminin chains have been identified. A rat B1 chain homologue, s-laminin (B1s), has been identified. A human A chain homologue, merosin (Am), has been described and is the same as a homologue A chain found in mouse and bovine heart. Both chains can combine with the laminin A, B1 or B2 chains to form the variant trimeric proteins [Ae, B1s, B2e], [Am, B1e, B2e] and [Am, B1s]. A second B1 variant (the sequence of which is a chain based on partial cDNA sequences) from avian eye has been reported and overlapping cDNAs for a human variant B2 chain called laminin B2t have also been described.

Kalinin is an epithelium-specific laminin variant that is the major, if not the only component of the anchoring filament. (The anchoring filament is a characteristic ultrastructural component of the dermal-epidermal junction of skin believed to mediate the adhesion of the epithelium to the basement membrane.) The kalinin molecule contains three disulfide bond-linked polypeptide chains consisting of a 200-kD kalinin A chain (Ak), a 155-kD kalinin B2 chain (B2t), and a 140-kD kalinin B1 chain (B1k). Rotary shadowing of the molecule results in a 107-nm rod with globular domains at each end.

Kalinin is an epithelial-specific cell attachment factor utilized by skin keratinocytes for strengthening their attachment to the underlying dermis. Antibodies to the Ak chain cause the detachment of subconfluent keratinocytes from their growth substrate and deepithelization of intact skin.

SUMMARY OF THE INVENTION

In general, the invention features a purified DNA including a sequence encoding a B1k chain of laminin.

In preferred embodiments: the DNA encodes the B1k protein of (SEQ ID NO:2); the encoded B1k peptide is at least 80, more preferably 90, and most preferably 95 or 98% homologous with the sequence of (SEQ ID NO:2); the DNA encodes a biologically active B1k.

In another aspect, the invention features a recombinant B1k.

In preferred embodiments: the recombinant B1k protein has the sequence of (SEQ ID NO:2); the recombinant B1k peptide is at least 80, more preferably 90, and most preferably 95 or 98% homologous with the sequence of (SEQ ID NO:2); the recombinant B1k has biological activity.

The invention also includes a vector including a DNA sequence encoding a B1k protein; a cell containing the vector; a method for manufacture of B1k including culturing the cell in a medium to express B1k.

In another aspect, the invention features a purified DNA including (or consisting essentially of) a sequence encoding a fragment of a B1k laminin chain.

In preferred embodiments: the sequence encodes domain VI of B1k, or a kalinin A chain-binding fragment thereof; the sequence encodes a peptide with a biological activity of domain VI of native B1k, e.g., the ability to bind to a kalinin A chain; the sequence encodes any of domain VI, V, IV, III, II, α, or I of B1k.

In other preferred embodiments: the sequence of the encoded B1k fragment is essentially the same as that of a naturally occurring B1k sequence; the DNA sequence which encodes the B1k fragment is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes a B1k fragment hybridizes under high or low stringency to a nucleic acid which encodes a naturally occurring B1k sequence e.g., the amino acid sequence of SEQ ID NO:1; the amino acid sequence of the encoded B1k fragment is less than 30, more preferably less than 40, more preferably less than 50, and most preferably less than 60, 80, 100, or 200 amino acid residues in length; the encoded B1k amino acid sequence is at least 50% more preferably 60%, more preferably 70%, more preferably 80%, more preferably 90%, and most preferably 95% as long as a naturally occurring B1k; the amino acid sequence of the encoded B1k fragment is at least 80%, more preferably at least 85%, yet more preferably at least 90%, yet more preferably at least 95%, and a most preferably at least 98 or 99% homologous with a naturally occurring B1k sequence, e.g., the sequence of SEQ ID NO:1; the fragment has biological activity.

In other preferred embodiments the fragment includes more than one B1k domain and: the domains in the encoded peptide are arranged in the same relative linear order as found in a naturally B1k; the linear order of the encoded domains is different from that found in a naturally occurring B1k; the domains in the encoded peptide differ in one or more of composition (i.e., which domains are present), linear order, or number (i.e., how many domains are present or how many times a given domain is present) from a naturally occurring B1k.

In another aspect, the invention features, a DNA, preferably a purified DNA, which includes (or consists essentially of) a sequence encoding a fragment of B1k of 20 or more amino acids in length, the peptide having at least 90% homology with an amino acid sequence which is the same, or essentially the same, as a naturally occurring B1k peptide, e.g., the amino acid sequence of SEQ ID NO:2. In preferred embodiments the purified DNA encodes: a peptide which is at least 30, more preferably at least 40, more preferably at least 50, and most preferably at least 60, 80, 100, or 200, amino acid residues in length; the encoded peptide is at least 50% more preferably at least 60%, more preferably 70%, more preferably 80%, more preferably 90%, and most preferably 95% as long as a naturally occurring B1k; a peptide which is at least 80, more preferably at least 85, yet more preferably at least 90, yet more preferably at least 95, and most preferably at least 98 or 99% homologous with an amino acid sequence which is the same, or essentially the same, as a naturally occurring B1k peptide, e.g., the amino acid sequence of SEQ ID NO 2; the peptide has biological activity.

The invention also includes a DNA sequence encoding a B1k fragment; a cell containing the purified DNA; a method for manufacture of a B1k fragment comprising culturing the cell in a medium to express the B1k fragment.

In another aspect, the invention features a peptide which is a fragment of a B1k laminin chain.

In preferred embodiments: the peptide includes (or consists essentially of) domain VI of B1k or a kalinin A chain-binding fragment thereof; the peptide has a biological activity of domain VI of native B1k, e.g., the ability to bind to a kalinin A chain; the peptide includes any of domain VI, V, IV, III, II, α, or I of B1k; the fragment has biological activity.

In other preferred embodiments: the sequence of the peptide is essentially the same as that of a naturally occurring B1k sequence; the DNA sequence which encodes the B1k peptide is at least 85%, more preferably at least 90%, yet more preferably at least 95%, and most preferably at least 98 or 99% homologous with DNA encoding a naturally occurring B1k, e.g., B1k encoding DNA from SEQ ID NO:1; the sequence which encodes the B1k peptide hybridizes under high or low stringency to a nucleic acid which encodes a naturally occurring B1k sequence e.g., the amino acid sequence of SEQ ID NO:2; the amino acid sequence of the peptide is less than 30, more preferably less than 40, more preferably less than 50, and most preferably less than 60, 80, 100, or 200 amino acid residues in length; the peptide's amino acid sequence is at least 50% more preferably 60%, more preferably 70%, more preferably 80%, more preferably 90%, and most preferably 95% as long as a naturally occurring B1k; the amino acid sequence of the peptide is at least 80%, more preferably at least 85%, yet more preferably at least 90%, yet more preferably at least 95%, and a most preferably at least 98 or 99% homologous with a naturally occurring B1k sequence, e.g., the sequence of SEQ ID NO:2.

In other preferred embodiments the peptide includes more than one B1k domain and: the domains in the peptide are arranged in the same relative linear order as found in a naturally B1k; the linear order of the domains is different from that found in a naturally occurring B1k; the domains in the peptide differ in one or more of composition (i.e., which domains are present), linear order, or number (i.e., how many domains are present or how many times a given domain is present) from a naturally occurring B1k; the peptide has biological activity.

In another aspect, the invention features a transgenic animal, e.g., a rodent, having a B1k transgene, e.g., a transgene which misexpresses the B1k chain of laminin.

In another aspect, the invention features a method of increasing the permeability of the skin including inhibiting an interaction between B1k and a second molecule, e.g., a kalinin A chain.

In preferred embodiments, the interaction is inhibited by: administering an antibody against a site on kalinin A with which B1k interacts; administering an antibody against a site on B1k, e.g., a site in domain VI, which interacts with the second molecule; administering a fragment of B1k, e.g., a fragment containing domain VI which competes, e.g., competitively or non-competitively with B1k for a site on the second molecule.

In another aspect, the invention features a method of promoting the adhesion of a molecule, e.g., kalinin A or kalinin A- containing molecule, e.g., kalinin or laminin or a cell, e.g., a keratinocyte, to a substrate including providing the substrate coupled, linked, or adhered, to a fragment of B1k which includes domain VI, contacting the molecule or cell, with the B1k domain VI.

In preferred embodiments, the method further includes forming a covalent bond, e.g., a sulfhydral bond, between the molecule or cell and the B1k domain VI.

In another aspect, the invention features a peptide useful for promoting the adhesion of a first molecule or cell, e.g., a keratinocyte, to a second molecule or cell, e.g., a keratinocyte, including a first B1k domain linked to a second B1k domain. (The first domain, e.g., domain VI, binds to the first molecule or cell and the second domain, e.g., domain VI, binds to the second molecule or cell).

In another aspect, the invention features a method of coupling a first molecule or cell to a second molecule or cell including providing a molecule having a first B1k domain and a second B1k domain, linking the first molecule or cell to the first domain, and linking the second molecule or cell to the second domain.

In preferred embodiments: the first and/or second molecule is an adhesion molecule, e.g., laminin, kalinin, or collagen; the first and/or second B1k domain is domain VI or a kalinin A chain-binding fragment thereof of B1k; the first and/or second cell in a keratinocyte.

The invention also includes substantially pure preparation of an antibody, preferably a monoclonal antibody directed against a B1k protein or a fragment of a B1k protein, e.g., a fragment which contains only one domain of B1k; a therapeutic composition including an B1k protein or fragment thereof and a pharmaceutically acceptable carrier; a therapeutic composition which includes a purified DNA of the invention and a pharmaceutically acceptable carrier.

In another aspect, the invention features a method for treating an animal, e.g., a human, a mouse, a transgenic animal, or an animal model for a disorder, e.g., a disorder of the dermis, e.g., epidermal bulosis, including administering a therapeutically-effective amount of a B1k or fragment thereof to the animal.

In another aspect, the invention features a method for treating an animal, e.g., a human, a mouse, a transgenic animal, or an animal model for a disorder, e.g., a disorder of the dermis, e.g., epidermal bulosis, including administering to the animal cells selected, e.g., selected in vitro, for the expression of a product of the B1k gene, e.g., cells transformed with B1k or B1k fragment-encoding DNA.

In preferred embodiments: the cells are taken from the animal to which they are administered; the cells are taken from an animal which is MHC matched with the animal to which they are administered; the cells are taken from an animal which is syngeneic with the animal to which they are administered; the cells are taken from an animal which is of the same species as is the animal to which they are administered.

In another aspect, the invention features a method for treating an animal, e.g., a human, a mouse, a transgenic animal, or an animal model for a disorder, e.g., a disorder of the dermis, e.g., epidermal bulosis, including administering to the animal a nucleic acid encoding a B1k or fragment thereof and expressing the nucleic acid.

In another aspect, the invention features a method of evaluating the effect of a treatment, e.g., a treatment designed to promote adhesion of a keratinocyte to its substrate including carrying out the treatment and evaluating the effect of the treatment on the expression of the B1k gene.

In preferred embodiments the treatment is administered: to an animal, e.g., a human, a mouse, a transgenic animal, or an animal model for a dermal disorder, e.g., epidermal bulosis, or to a cell, e.g., a cultured cell.

In another aspect, the invention features a method for determining if a subject, e.g., a human, is at risk for a disorder related to mis-expression of the B1k gene, e.g., a disorder of the dermis, e.g., epidermal bulosis, including examining the subject for the expression of the B1k gene, non-wild type expression or mis-expression being indicative of risk.

In another aspect, the invention features a method for determining if a subject, e.g., a human, is at risk for a disorder related to mis-expression of the B1k gene, e.g., a disorder of the dermis, e.g., epidermal bulosis, including providing a nucleic acid sample from the subject and determining if the structure of an B1k gene allele of the subject differs from wild type.

In preferred embodiments: the determination includes determining if an B1k gene allele of the subject has a gross chromosomal rearrangement; the determination includes sequencing the subject's B1k gene.

In another aspect, the invention features, a method of evaluating an animal or cell model for a disorder, e.g., a disorder of the dermis, e.g., epidermal bulosis, including determining if the B1k gene in the animal or cell model is expressed at a predetermined level or if the B1k gene is mis-expressed. In preferred embodiments: the predetermined level is lower than the level in a wild type or normal animal; the predetermined level is higher than the level in a wild type or normal animal; or the pattern of isoform expression is altered from wildtype.

In another aspect, the invention features a transgenic rodent, e.g., a mouse, having a transgene which includes an B1k gene or B1k protein encoding DNA. In preferred embodiments: the B1k gene or DNA includes a deletion, e.g. a deletion of all or part of B1k, e.g., a deletion of all or part of a domain e.g., domain VI, or is otherwise mis-expressed.

Purified DNA is DNA that is not immediately contiguous with both of the coding sequences with which it is immediately contiguous (i.e., one at the 5' end and one at the 3' end) in the naturally occurring genome of the organism from which the DNA of the invention is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA or a genomic DNA fragment produced by PCR or restriction endonuclease treatment) independent of other DNA sequences. It also includes a recombinant DNA which is part of a hybrid gene encoding additional polypeptide sequence.

Homologous refers to the degree of similarity in sequence between two polypeptide molecules or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, 6 of 10, of the positions in two sequences are matched or homologous then the two sequences are 60% homologous. By way of example, the DNA sequences ATTGCC and TATGGC share 50% homology.

A transgene is defined as a piece of DNA which is inverted by artifice into a cell and becomes a part of the genome of the animal which develops in whole or part from that cell. Such a transgene may be partly or entirely heterologous to the transgenic animal.

A transgenic animal, e.g., a transgenic mouse, is an animal having cells that contain a transgene, which transgene was introduced into the animal, or an ancestor of the animal, at a prenatal, e.g., an embryonic stage.

A substantially pure preparation of a peptide is a preparation which is substantially free of the peptides with which it naturally occurs in a cell. A substantially pure preparation of a non-naturally occurring peptide is one which is at least 10% by weight of the peptide of interest.

Mis-expression, as used herein, refers to a non-wild type pattern of gene expression. It includes: expression at non-wild type levels, i.e., over or under expression; a pattern of expression that differs from wild type in terms of the time or stage at which the gene is expressed, e.g., increased or decreased expression (as compared with wild type) at a predetermined developmental period or stage; a pattern of expression that differs from wild-type in terms of the tissue specificity of expressions, e.g., increased or decreased expression (as compared with wild-type) in a predetermined cell type or tissue type; a pattern of expression that differs from wild type in terms of the length, amino acid sequence, post-translational modification, or a biological activity of a B1k gene product; a patterns of expression that differs from wild-type in terms of the effect of an environmental stimulus or extracellular stimulus on expression of the gene, e.g., a pattern of increased or decreased expression (as compared with wild type) in the presence of an increase or decrease in the strength of the stimulus; or a pattern of isoform expression which differs from wild-type.

A protein or peptide has B1k biological activity if it has one or more of the following properties: the ability to covalently bind via disulfide bond formation with a kalinin B2 chain and a kalinin A chain to form a trimeric protein, kalinin; the ability to bind the kalinin A chain through a covalent disulfide bond formation with domain VI of the B1k chain; the ability to specifically bind type IV collagen; if a B1k domain present on a B1k protein or fragment has a biological property that the domain has when present in the native B1k molecule, e.g., the ability to bind or associate in a specific way with another molecule, e.g., another laminin or kalinin chain or the ability to form a characteristic native rotary shadowy structure characteristic of native B1k.

The molecules of the invention are useful for promoting adhesion of adhesion molecules or keratinocytes to a substrate, e.g., human dermis. The molecules of the invention are also useful for research in cell adhesion. The role of the DNA sequence encoding a peptide having B1k activity and its products can be studied in cells, e.g., cultured cells, transformed with the aforementioned DNA sequence, or fragments thereof, or in transgenic animals. The peptides fragments of the invention allow preparation of antibodies, i.e., monoclonal antibodies, directed against a specific domain.

Other features and advantages of the invention will be apparent from the following description and from the claims.

DETAILED DESCRIPTION

DRAWINGS

The drawings are first briefly described.

Figure 1:
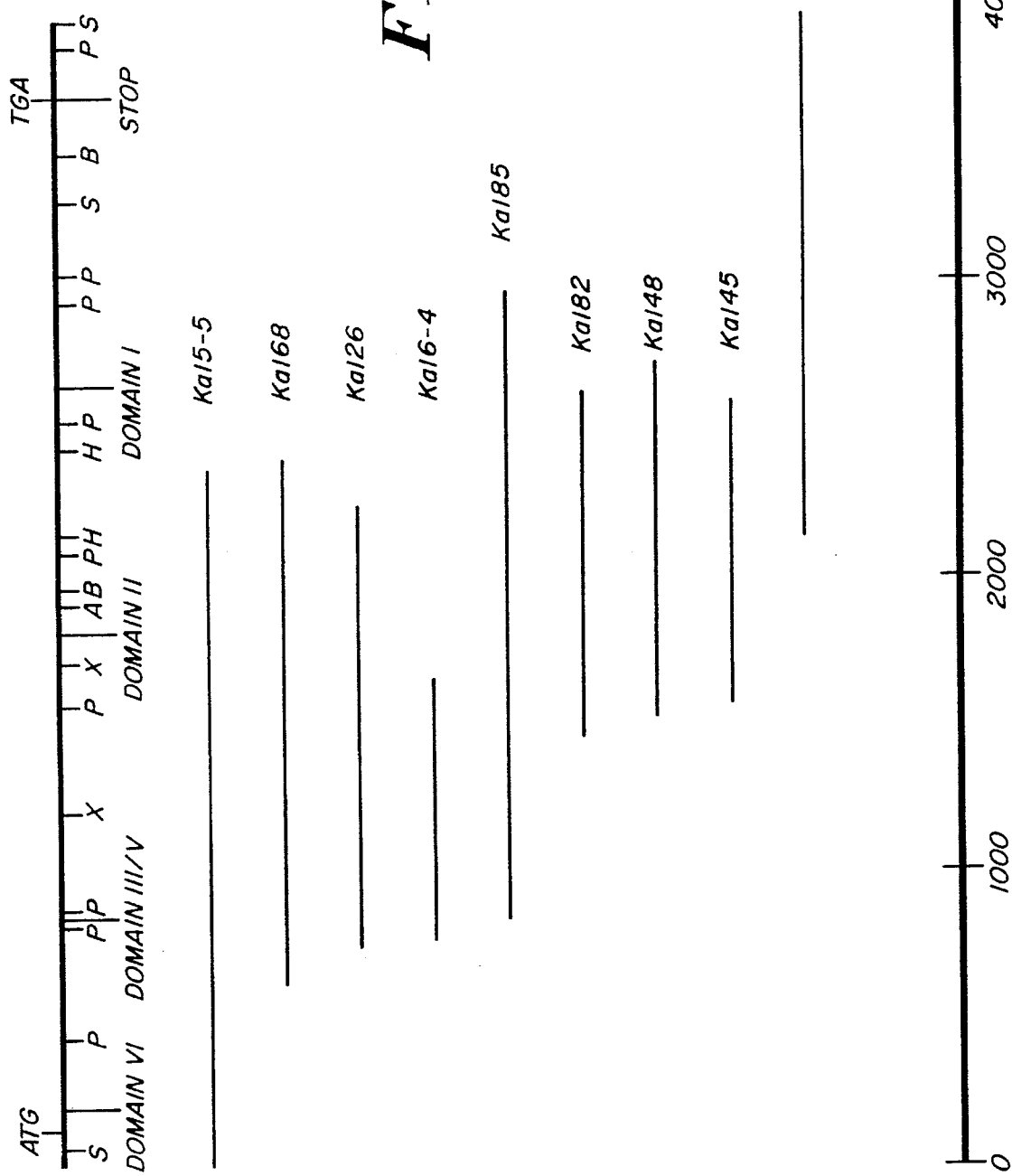

FIG. 1 is a map of the B1k region showing (heavy line) start (ATG) and stop codons (TGA), restriction sites (single letter abbreviations), and domains. The light lines below the map show overlapping cDNA clones encoding the entire kalinin B1 chain.

FIG. 2–2C is a map of the nucleotide sequence of the laminin B1k chain (SEQ ID NO: 1) and the predicted amino acid sequence (SEQ ID NO: 2) of the B1k peptide chain. Triangles indicate potential N-linked glycosylation sites. Stars indicate potential glycosaminoglycan attachment sites. Potential O-linked glycosilation sites are underlined.

FIG. 3A–3D, is a domain-by-domain comparison of the amino acid sequences of the laminin B1k chain (SEQ ID NO: 3) and the human B1 (SEQ ID NO: 4) chain (B1e).

Figure 4:
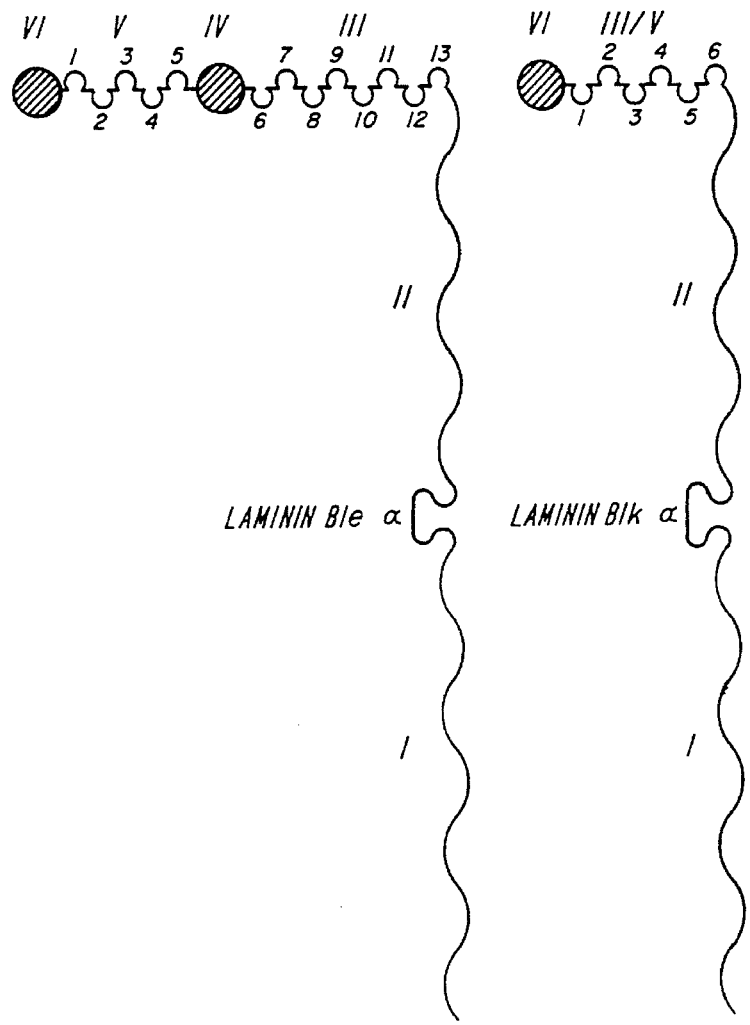

FIG. 4 is: A) a comparison of the domain sizes and percent identity for the various domains of the laminin B1e and laminin B1k chains; and B) a depiction of the numbering scheme for the laminin B1k domains. The domains are numbered according to their similarity to the comparable domains in the laminin B1e chain. Some of the laminin B1e chain domains are missing in the laminin B1k chain and those that remain are truncated in comparison to the laminin B1e chain.

FIG. 5 is a comparison of the amino acid sequences of domain VI for B1k (SEQ ID NO: 5), B1e (SEQ ID NO: 6), and B1s (SEQ ID NO: 7). The underlined regions are areas where the sequence identity between B1e and B1s is above average, but the sequence identity with B1 is considerably less than average. The arrow shows an additional cysteine contained by B1k at residue number 50.

FIG. 6 is a comparison of peptide sequences of rat laminin B1s (SEQ ID NO: 8), human laminin B1s (SEQ ID NO: 9) and human laminin B1k (SEQ ID NO: 10). Also shown is a comparison of the amino acid sequences of human laminin B2t peptides determined by deduction from cDNA (SEQ ID NO: 11 and SEQ ID NO: 13) (top line) and from sequencing of purified peptide (bottom line) (SEQ ID NO: 12 and SEQ ID NO: 14).

FIG. 7 is a comparison of the cloned cDNA sequence to the B1 and B2 chains of laminin (LAMB1e and LAMB2e), the B2 chain of kalinin (LAMB2t) and the B1 chain of s-laminin (LAMB1s).

cDNA Clones for the Kalinin B1 (Laminin B1k) Chain

The screening of the squamous cell carcinoma cell cDNA expression library with a polyclonal antibody which recognizes human kalinin yielded several positive clones. The fusion proteins from positive clones were adsorbed to nitrocellulose and exposed to the polyclonal antiserum used for the initial screening. Antibodies binding the fusion proteins were individually collected and used for Western blot analysis of partially purified kalinin. Clones were identified that expressed fusion proteins that bound antibodies specific for the 140-kD and the 155/105-kD chain. (The B2 chain is processed from a 155 to a 105 kD form.) Selected clones were sequenced and the predicted amino acid sequences encoded by the cDNAs showed extensive homologies with the B1 and B2 laminin chains. The encoded sequences from the B1k and B2t chains were confirmed by direct amino acid sequencing of the 140-kD and 155/105-kD kalinin chains.

The nucleotide sequences of the 155/105-kD chain were 99.9% identical to the recently published B2t chain and 100-kD chain of nicein. Protein sequencing of two tryptic peptides from the chain exactly matched derived amino acid sequences, confirming that laminin B2t, the 100-kD nicein chain and the 155/105-kD kalinin chain are identical.

Clones encoding the kalinin 140-kD kalinin B1 chain were selected for further characterization (Kal26, Kal45, Kal48, Kal68, Kal82, and Kal85, FIG. 1). These clones contained 1.5-kb, 0.9-kb, 1.3-kb, 1,8-kb, 1.2-kb, and 2.1-kb inserts, respectively, and nucleotide sequencing demonstrated that the derived amino acid sequences showed extensive similarity to human laminin B1 chain. Rescreening of the cDNA library with Kal45 resulted in the isolation of clones Kal5-5 and Kal6-4 (FIG. 1). These clones contained 2.3-kb and 1.0-kb inserts, respectively. To obtain the 3' end of the cDNA, a 3' RACE procedure (BRL) was used on total mRNA from squamous cell carcinoma media. This resulted in the clone Kal92-1 (1.8-kb). The complete nucleotide sequence of the overlapping clones and the predicted amino acid sequence are shown in FIG. 2.

The immunogen for polyclonal antiserum against kalinin purified from human keratinocyte-conditioned culture medium has been previously described (Lunstrum et al., 1986; Rousselle et al., 1991).

Isolation of RNA and cDNA synthesis were performed as follows. Ten Costar T-225 flasks were seeded with squamous carcinoma cells (SCC) and allowed to grow until subconfluent. Media was removed and the cells were lysed and total RNA isolated following the guanidium thiocyanate method of Chomczynski and Sacchi, 1987. Poly A+RNA was collected using a Collaborative Research oligo dT Cellulose type 3 column and following company guidelines. Six hundred mg of Poly A+ enriched RNA was sent to Clontech Laboratories (Palo Alto, Calif.) for construction of the Lambda gt11 cDNA library using random primers.

Library screening was performed as follows. The anti-kalinin polyclonal antibody (pAB) was diluted in 1:10 in 10 mM TNT (Tris-HCl, pH 8.0; 150 mM NaCl; 0.05% Tween 20; 3% BSA). E. coli (Y-1090 strain) whole cell lysate was added to the diluted antibody and incubated at 4° C. for 24 hours on a nutator. The pre-absorbed antibody was centrifuged at 10,000 rpm for 10 minutes at 4° C. and the supernatant collected. The absorbed antibody was then diluted 1:10 (final dilution 1:100) in TBST (50 mM Tris-HCl, pH 7.9; 150 mM NaCl; 0.05% Tween 20) and 1.2% BSA added. The diluted absorbed antibody was used to screen $8.34 \times 10^5$ plaques from the unamplified random-primed cDNA library and horseradish peroxidase (HRP) secondary antibody was used to visualize the positive plaques. A total of 89 positive individual plaques were purified in a larger scale and tested again against the antibody.

Epitope determination for phage clones were performed as follows. For each clone, three 150×15 mm LB-ampicillin plates were plated at a density of 6000 pfu and grown 3 hours at 37° C. The plates were overlaid with IPTG saturated nitrocellulose filters and incubated overnight at 37° C. Plates were cooled at 4° C. for 15 minutes and the filters were removed and washed 3 times in TBST (15 min for each wash). The filters were blocked in 4% BSA in TBST for 1 hour at room temperature (RT). Filters were then washed 3 times in TBST. Filters were exposed to the pAB for 3–4 hours at RT followed by 3 washes in TBST. The antibody was eluted from the filter by soaking each filter in 25 ml of 1M acetic acid for 20 minutes. The antibody/acetic acid solution for each of the triplicate samples was pooled and 2 drops of a saturated phenol red solution was added. The solution was neutralized by the addition of an aqueous solution saturated with Tris-HCl and 0.03% BSA was added. The solution was dialyzed against two changes of 1×TBS at 4° C. overnight. The purified antibody solution was collected from the dialysis membrane and a "pinch" of BSA was added. The solution was frozen at −20° C. until needed.

Mini-western blots of purified kalinin were made and exposed to purified antibody from each of the clones for 60-hours at 4° C. Blots were then washed three times in TBST for 15 minutes each. Secondary HRP conjugated antibody was used to illuminate the particular band of kalinin chain corresponding to the clone.

Northern blots were performed as follows. Poly A+RNA was isolated from cell culture of 2 T165 flasks of 70–80% confluent squamous carcinoma cells using Invitrogen's Fast Track RNA isolation systems and exactly following the manufacturer's recommendations. The final RNA pellet was resuspended in 50 ml elution buffer. Twenty mb of Poly A+RNA was used for the gel and subsequent blot using the procedure outlined by Foumey et al. Clone Kal5-5 was radioactively labeled with the Amersham Random labeling system. The blot was placed against X-ray film for 2 hours at −80° C.

3' Rapid Amplification of cDNA Ends (RACE) was performed as follows. A 3' RACE kit was purchased from GIBCO BRL and 1 mg poly A+RNA in 13 ml DEPC-treated water was made into cDNA by reverse transcriptase according to manufacturer's recommendations. The first strand DNA was amplified by PCR following the manufacturer's protocol using the provided antisense poly (T) primer called AP and a specific sense primer for the kalinin B1 chain called D92 (GCT TCA ATG GTC TCC TTA CTA TGT A) (SEQ ID NO: 15).

The Laminin B1k Chain Encodes a Distinct Laminin-like Polypeptide

Analysis of the sequence showed that the first possible translated methionine (first amino acid residue, FIG. 2) is followed by a stretch of hydrophobic amino acid residues which are typical for a signal peptide. From the formula for a signal peptide (von Heijne, 1983 and 1986), the signal peptide would be cleaved following Ala17. The 17 residue long signal peptide is followed by an open reading frame of 1148 amino acid residues with a deduced molecular weight of 126,464 daltons. There are 3 putative N-linked glycosylation sites having the predicted residue sequence Asn-X-Ser/Thr, 3 potential O-linked glycosylation sites having the predicted cluster of three or more consecutive Ser and Thr residues and 2 potential glycosaminoglycan attachment consensus sequences, Ser-Gly-X-Gly. In addition there are 120 nucleotides of 5' untranslated sequences and 315 nucleotides of 3' untranslated sequences for a total of 3931 bases. Northern blot analysis showed a single message of 4.0-kb when probed with the cDNA clone Kal5-5.

Protein Sequencing was performed generally as according to Aebersold et al., 1987. Kalinin purified from amnion (Marinkovich et al., 1992a) was run on a polyacrylamide gel in the presence of 2-mercaptoethanol and blotted on a nitrocellulose membrane (Biorad). The 140-kD band was excised and digested by the protease Lys-C. The digested product was separated by HPLC and one fragment was sequenced on an Applied Biosystem sequencer. Computer analysis of the mature polypeptide demonstrated that the laminin B1k chain is most similar to the human laminin B1 chain (LamB1E). A comparison of the laminin B1k polypeptide to this chain is presented in FIG. 3.

Pyroglutamate aminopeptidase reaction was performed generally as according to Andrews et al., 1991. Briefly, kalinin purified from amnion was run on a polyacrylamide gel in presence of 2-mercaptoethanol and blotted on a PVDF membrane in 25 mM Tris, 192 mM glycine, 0.05% SDS and 10% methanol for 4 hours. The 140-kD band was excised, blocked in PVP-40 in 0.1M acetic acid at 37° C. for 30 minutes, washed ten times in water and digested by pyroglutamate aminopeptidase (Boehringer Mannheim) (62.5 mg/mg of protein in 50 mM sodium phosphate, 10 mM EDTA, 5 mM DTT, 5% glycerol, pH 8.0) for 12 hours at 4° C. An additional 62.5 mg of pyroglutamate aminopeptidase/mg of protein was added and digestion was done for 12 hours at 37° C. The blot was washed ten times in water, dried under vacuum and subjected to sequencing on an Applied Biosystem sequencer.

Domain Structure of the Laminin B1k Chain

Since the laminin B1k chain has similarity to the laminin B1e chain, its domains were assigned numbers according to their similarity to the comparable domains in laminin (FIG. 4A). Some of the laminin B1e chain domains are missing in the laminin B1k chain and those that remain are all truncated in comparison to the laminin B1e chain. Specifically, the carboxy-terminal ⅓ of domain V, all of domain IV, and the amino-terminal ⅔ of domain III are missing in the laminin B1k chain. FIG. 4A shows a comparison of the domain sizes and percent identity for the various domains of the laminin B1e and laminin B1k chains. The most amino-terminal domain, domain VI (residues 1–231), is a 231-amino acid residue region containing 9 cystine residues. This domain is likely to form a globular structure similar to domain VI in the laminin B1e chain. Domain III/V (residues 232–559) contains six cysteine-rich EGF modules with three of them similar to comparable modules in domain III (EGF 1, 2, and 3) and three of them similar to comparable modules in domain V (EGF 11, 12, 13) of the laminin B1e chain. The laminin B1k chain has no globular domain IV as is found in the laminin B1e chain. Domain II (residues 560–766), as in the laminin B1e chain, begins with two closely spaced cysteins and is predicted to be an α-helical domain containing heptad repeats typical for coiled-coil proteins. Domain I (residues 798–1148) also contains heptad repeats typical for coiled-coil proteins. Just as in laminin B1e, this domain contains a single cysteine residue one residue away from the carobxyl-terminal end. Also similar to the laminin B1e chain is a cysteine-rich (6 cysteine residues) a domain that interrupts the helical structures of domains I and II.

Since domain VI is the only globular domain retained by the B1k chain, and since the homologous domain in laminin and s-laminin are believed to mediate self-assembly, the sequences domain VI for B1k, B1e and B1s were compared (FIG. 5). The amino acid identity of domain VI for B1e and B1s shows 70% sequence conservation (FIG. 5). The number and location of cysteinyl residues is identical. Comparisons of the B1k sequence with these two chains shows 49.8% overall sequence identity. As shown in FIG. 5, B1e and B1s contain several regions within domain VI where the sequence identity is above average. Three of these regions share considerably less than average sequence identity with the B1k chain (FIG. 5, underlined). The B1k chain contains an additional cysteine at amino acid residue number 50 (FIG. 5, arrow). This region is also highly divergent from the B1e and B1s chains with an 18% amino acid residue identity to the B1e chain (excluding the obligatory cysteine) whereas, the same region is 70% identical between B1e and B1s. These comparisons suggest that B1k shares an overall structural similarity with B1e and B1s, but the chains are likely to be functionally divergent.

The Laminin B1k Chain Is a Truncated Chain

As described above, overlapping cDNA clones encoding the entire 140-kD laminin B1k chain were characterized.

The 3.9-kb sequenced corresponds well with the 4.0-kb message size predicted by northern blot analysis. 3' and 5' RACE procedures and were not able to extend the sequence further on either end.

The identity of the cDNAs were confirmed by sequencing a 19-residue long tryptic peptide from the purified 140-kD laminin B1k chain (double-underlined in FIG. 2). Additional protein sequencing of the amino-terminal end of the polypeptide chain confirmed that the end was blocked and therefore most likely began with the residue Gln. After unblocking the end we determined the partial sequence Q-A-C-X-R (X is an indeterminate residue) which corresponds well with our predicted signal peptide cleavage site (start of domain VI, FIG. 2).

The estimated protein size from the cDNAs is 126,464 daltons. This is in contrast to protein data which predicts a protein of about 140,000 daltons. The most likely explanation for this discrepancy is that the chain is glycosylated. There are three potential O-linked glycosylation sites which are underlined in FIG. 2. There are two potential glycosaminoglycan attachment sites marked with stars and three potential N-linked glycosylation sites marked by triangles in FIG. 2. It is interesting to note that the three potential O-linked glycosylation sites are all located in the amino-terminal globular domain, domain VI, which rotary shadowed images predicts to project from the long arm, an ideal position to interact with other molecules such as carbohydrates. In addition, one N-linked glycosylation site is present in the α domain which may extend away from the long arm of the chain and interact with other molecules. The function of the α domain is not known.

The Laminin B1k Chain Is Similar To The Laminin B1e and Laminin B1s Chains

FIG. 7 shows a comparison of our cDNA sequence to the B1 and B2 chains of laminin (LAMB1E and LAMB2E), the B2 chain of kalinin (LAMB2T) and the B1 chain of s-laminin (LAMB1S). Since the kalinin B1 chain is clearly related to these other laminin subunits, the convention of Engel et al., 1991 was followed and the Kalinin B1 chain will be named Laminin B1k. As is apparent from FIG. 7, the human laminin B1k chain is most similar to the human laminin B1e (34.1% identity) and rat laminin B1s (37.1% identity) chains. Initially it seemed possible that the laminin B1k chain might be the human equivalent of the laminin B1s chain since the amino acid residue identity was high when considering comparing two different species. There are two pieces of evidence that show that the laminin B1k chain is distinct from the laminin B1s chain. The first is the size of the laminin B1k chain polypeptide which was previously reported to be 140-kD. The laminin B1s chain in rat is about 190-kD which is only slightly smaller than the 200-kD laminin B1e chain. Since there is good conservation of protein size between species (from human to drosophila) for all three of the laminin chains (Laminin Ae, B1e, and B2e), one expects the same will hold true between species for the laminin B1s chain as well and it is predicted that this chain will be 190–200-kD in size. Additional evidence that the laminin B1k chain is distinct from the laminin B1s chain is the fact that a human tryptic peptide sequence was found that is not found in the laminin B1k chain, but has 95.8% identity to the rat laminin B1s chain.

Since the human sequence of the laminin B1s chain is not available, the B1k sequence was compared to the most well described similar molecule, the laminin B1e chain. The major difference between the laminin B1e and laminin B1k chains is their size. The laminin B1k chain has a truncated structure and, therefore, a lower molecular mass than the 200-kD laminin B1e chain. This smaller size is mainly due to the absence of the globular domain which corresponds to domain IV in the laminin B1e chain and to the fact that the corresponding domains III and V are fused into a single domain that is about half the size of the two domain together. There may also be differences in glycosylation between the two polypeptides.

As was found for the laminin B2t chain, the short arms of laminin B1k and laminin B1e have the greatest sequence homology than the long arms (FIG. 4, upper panel: compare domains III–VI, 40–50% identity, to domains I–II, 20–30% identity).

Domain Structure Of The Short Arm Of The Laminin B1k Chain

The greatest functional significance of the short arm is found in the amino-terminal domain VI. In laminin B1e, domain VI has been reported to aid in the self-assembly of the laminin molecules in vitro. The presence of this domain in the laminin B1k chain suggests that this domain could help to organize the extracellular matrix by associating with either other kalinin or laminin molecules. Since this domain is missing in laminin B2t, if the laminin protein associates with other molecules, then this domain is especially crucial in laminin B1k. One possible ligand for this domain is the recently described K-laminin molecule which contains the laminin B1e and B2e chains and a novel A chain. A second candidate for the interaction is type IV collagen which has been reported to bind to the short arms of the laminin B chains.

The comparison of the B1k sequence to B1e and B1s within the VI domain are particularly interesting. The highly divergent amino acid residue identity in certain areas (FIG. 5, underlined) strongly suggests that domain VI of B1k is functionally different from the other known laminin B1 chains. B1k domain VI also contains an odd number of cysteine residues (FIG. 6, arrow), suggesting that one of these is unpaired and available to stabilize interactions of domain VI with another entity. These observations support the hypothesis that kalinin is unlikely to self-assemble through interactions of the VI domains, but rather, the VI domain specifically interacts with the A chain of K-laminin. In tissues, kalinin is disulfide bonded to K-laminin, but not to other laminins that do not contain the K-laminin A chain. Rotary-shadowed images of the adduct suggest that the short arm region of kalinin associates at the crotch of the K-laminin short arms. Since the B1k chain is the only kalinin chain that remains unprocessed in the mature kalinin molecule, the association with K-laminin appears to be mediated by the B1k chain. The significant diversion in sequence homology between the VI domains of B1k versus B1e and B1s, and the presence of a potentially unpaired cysteine residue are consistent with the concept that the B1k VI domain binds the short arm of the K-laminin A chain enabling alignment of an unpaired cysteine in each molecule and subsequent disulfide bond formation.

Domain IV is missing in the laminin B1k chain and while no functions have been reported for the comparable domain in the laminin B1e chain, some investigators reported small peptide sequences in this area can bind to heparin. Since the entire domain is absent in kalinin these sequences are missing.

Two cell-surface binding peptide sequences (PDSGR and YIGSR) have been reported in the EGF repeat number 9 in domain III of the laminin B1e chain. These peptide sequences are not present since the EGF repeats numbered 6–10 are all missing in domain III of the laminin B1k chain.

Domain Structure Of The Long Arm Of The Kalinin B1 Chain

The long arm of the laminin B1k chain contains numerous heptad-repeats similar to those found in the two B chains of laminin. The laminin B1e and B2e chains have been found to associate with one another and are in fact disulfide-bonded. Clearly the three chains of kalinin are disulfide-bonded since they can only be separated by gel electrophoresis only after reduction by β-mercaptoethanol. The 155-kD kalinin chain is known to correspond to the previously reported truncated laminin B2t chain by the cDNAs discussed herein as well as to sequenced tryptic peptides (FIG. 7). The laminin B1k chain appears to interact with the laminin B2t chain by forming an α-helix as is found between the laminin B1e and B2e chains and in fact computer analysis predicts that laminin B1k can form an α-helical coiled-coil structure just as laminin B1e. The laminin B1k and the laminin B2t chain each have a single cysteine in their carboxy-terminal regions that are candidates for disulfide-bonding. The laminin B1k chain also has the short cysteine-rich α domain that divides domains I and II and is predicted to stick out from the long-arm and perform as yet unknown functions.

Finally, adhesion of ciliary ganglion neurons has been attributed to the specific sequence LRE in the laminin B1s chain. This sequence is not found in the laminin B1k chain and this function would therefore be missing.

Other Embodiments

Nucleic acid encoding all or part of the B1k chain can be used to transform cells. For example, the B1k gene, e.g., a mis-expressing or mutant form of the B1k gene, e.g., a deletion, or DNA encoding a B1k chain can be used to transform a cell and to produce a cell in which the cell's genomic B1k gene has been replaced by the transformed gene, producing, e.g., a cell deleted for the B1k gene. Such cells can be used with cells capable of being gown in culture, e.g., cultured stem cells, to investigate the function of the B1k gene.

Analogously, nucleic acid encoding all or part of the B1k gene, e.g., a mis-expressing or mutant form of the gene, e.g., a deletion, can be used to transform a cell which subsequently gives rise to a transgenic animal. This approach can be used to create, e.g., a transgenic animal in which the B1k gene is, e.g., inactivated, e.g., by a deletion. Homozygous transgenic animals can be made by crosses between the offspring of a founder transgenic animal. Cell or tissue cultures can be derived from a transgenic animal and the in vivo effects of the laminin B1k chain can subsequently be studied.

The invention includes any fragment of B1k, or any recombinantly produced B1k or fragment thereof which is substantially homologous to a B1k protein, e.g., the B1k protein shown in FIG. 2, or other isoforms. Also included are: allelic variations; natural mutants; induced mutants, e.g., in vitro deletions; proteins encoded by DNA that hybridizes under high or low (e.g., washing at 2×SSC at 40° C. with a probe length of at least 40 nucleotides) stringency conditions to a nucleic acid naturally occurring (for other definition of high and low stringency see Current Protocols in Molecular Biology, John Wiley & Sons, New York, 1989, 6.3.1–6.3.6, hereby incorporated by reference); and polypeptides or proteins specifically bound by antisera to a B1k protein, especially by antisera to the active site or binding domain of a B1k protein. The term also includes chimeric polypeptides that include a B1k protein.

DNA and peptide sequences of the invention can be, e.g., mouse, primate, e.g., human, or non-naturally occurring sequences.

The invention also includes any biologically active fragment or analog of a B1k protein. By "biologically active" is meant possessing any in vivo or in vitro activity which is characteristic of B1k, e.g., B1k activity as described above. Because the B1k protein exhibits a range of physiological properties and because such properties may be attributable to different portions of the B1k protein molecule, a useful B1k protein fragment or B1k protein analog is one which exhibits a biological activity in any one (or more) of a variety of B1k protein assays, for example, the ability to bind the laminin Ak chain, as described above. A B1k protein fragment or analog possesses, most preferably 90%, preferably 40%, or at least 10%, of the activity of a naturally occurring B1k isoform, e.g., of the B1k protein shown in FIG. 2, in any in vivo or in vitro B1k assay.

Preferred analogs include B1k peptides or recombinant B1k proteins or peptides (or biologically active fragments thereof) whose sequences differ from the wild-type sequence by one or more conservative amino acid substitutions or by one or more non-conservative amino acid substitutions, deletions, or insertions which do not abolish biological activity. Conservative substitutions typically include the substitution of one amino acid for another with similar characteristics, e.g., substitutions within the following groups: valine, glycine; glycine, alanine; valine, isoleucine, leucine; aspartic acid, glutamic acid; asparagine, glutamine; serine, threonine; lysine, arginine; and phenylalanine, tyrosine. Other conservative substitutions can be taken from the table below.

| CONSERVATIVE AMINO ACID REPLACEMENTS | | |
|---|---|---|
| For Amino Acid | Code | Replace with any of |
| Alanine | A | D—Ala, Gly, beta-Ala, L—Cys, D—Cys |
| Arginine | R | D—Arg, Lys, D—Lys, homo-Arg, D-homo-Arg, Met, Ile, D—Met, D—Ile, Orn, D—Orn |
| Asparagine | N | D—Asn, Asp, D—Asp, Glu, D—Glu, Gln, D—Gln |
| Aspartic Acid | D | D—Asp, D—Asn, Asn, Glu, D—Glu, Gln, D—Gln |
| Cysteine | C | D—Cys, S—Me—Cys, Met, D—Met, Thr, D—Thr |
| Glutamine | Q | D—Gln, Asn, D—Asn, Glu, D—Glu, Asp, D—Asp |
| Glutamic Acid | E | D—Glu, D—Asp, Asp, Asn, D—Asn, Gln, D—Gln |
| Glycine | G | Ala, D—Ala, Pro, D—Pro, β-Ala Acp |
| Isoleucine | I | D—Ile, Val, D—Val, Leu, D—Leu, Met D—Met |
| Leucine | L | D—Leu, Val, D—Val, Leu, D—Leu, Met, D—Met |
| Lysine | K | D—Lys, Arg, D—Arg, homo-Arg, D-homo-Arg, Met, D—Met, Ile, D—Ile, Orn, D—Orn |
| Methionine | M | D—Met, S—Me—Cys, Ile, D—Ile, Leu, D—Leu, Val, D—Val |
| Phenylalanine | F | D—Phe, Tyr, D—Thr, L-Dopa, His, D—His, Trp, D—Trp, Trans-3,4, or 5-phenylproline, cis-3,4, or 5-phenylproline |
| Proline | P | D—Pro, L—I-thioazolidine-4-carboxylic acid, D— or L-1-oxazolidine-4-carboxylic acid |
| Serine | S | D—Ser, Thr, D—Thr, allo-Thr, Met, D—Met, Met(O), D—Met(O), L—Cys, D—Cys |
| Threonine | T | D—Thr, Ser, D—Ser, allo-Thr, Met, D—Met, Met(O), D—Met(O), Val, D—Val |
| Tyrosine | Y | D—Tyr, Phe, D—Phe, L-Dopa, His, D—His |
| Valine | V | D—Val, Leu, D—I,eu Ile, D—Ile, Met, D—Met |

Other useful modifications include those which increase peptide stability; such analogs may contain, for example, one or more non-peptide bonds (which replace peptide bonds) or D-amino acids in the peptide sequence.

Analogs can differ from a naturally occurring B1k protein in amino acid sequence or can modified in ways that do not affect sequence, or both. Analogs of the invention will generally exhibit at least 70%, more preferably 80%, more preferably 90%, and most preferably 95% or even, 99%, homology with a segment of 20 amino acid residues, preferably more than 40 amino acid residues or more preferably the entire sequence of naturally occurring B1k protein sequence.

Alterations in primary sequence include genetic variations, both natural and induced. Also included are analogs that include residues other than naturally occurring L-amino acids, e.g., D-amino acids or non-naturally occurring or synthetic amino acids, e.g.,β or γ amino acids. Alternatively, increased stability may be conferred by cyclizing the peptide molecule.

Nonsequence modification include in vivo or in vitro chemical derivatization or polypeptides, e.g., acetylation, methylation, phosphorylation, carboxylation, or glycosylation; glycosylation can be modified, e.g., by modifying the glycosylation patterns of a polypeptide during its synthesis and processing or in further processing steps, e.g., by exposing the polypeptide to glycosylation-affecting enzymes derived from cells that normally provide such processing, e.g., mammalian glycosylation enzymes; phosphorylation can be modified by exposing the polypeptide to phosphorylation-altering enzymes, e.g., kinases or phosphatases.

Fragments of B1k proteins or peptides can be made by methods known to those skilled in the art, e.g., by expressing B1k DNA which has been manipulated in vitro to encode the desired fragment; e.g., by restriction digestion or other manipulation of a B1k DNA e.g., the sequence in FIG. 2. Analogs can be made by methods known to those skilled in the art,, e.g., by in vitro DNA sequence modifications of the sequence of a B1k DNA e.g., the sequence in FIG. 2. For example, in vitro mutagenesis can be used to convert the DNA sequence of FIG. 2 into a sequence which encodes an analog in which one or more amino acid residues has undergone a replacement, e.g., a conservative replacement as described in the table of conservative amino acid substitutions provided herein. Fragments or analogs can be tested by methods known to those skilled in the art for the presence of B1k activity.

Also included are B1k protein polypeptides containing residues that are not required for biological activity of the peptide, such as residues that are not required for the biological activity of the polypeptide, or that result from alternative mRNA splicing or alternative protein processing events.

The invention also includes nucleic acids encoding the polypeptides of the invention.

In order to obtain a B1k protein, or fragment thereof, one can insert B1k-encoding DNA into an expression vector, introduce the vector into a cell suitable for expression of the desired protein, and recover and purify the desired protein by prior art methods. Antibodies to B1k proteins can be made by immunizing an animal, e.g., a rabbit or mouse, and recovering anti-B1k antibodies by prior art methods.

Other embodiments are within the following claims.

SEQUENCE LISTING ( 1 ) GENERAL INFORMATION:

( i i i ) NUMBER OF SEQUENCES: 14

( 2 ) INFORMATION FOR SEQ ID NO:1:

( i ) SEQUENCE CHARACTERISTICS:
( A ) LENGTH: 3931 base pairs
( B ) TYPE: nucleic acid
( C ) STRANDEDNESS: single
( D ) TOPOLOGY: linear ( i i ) MOLECULE TYPE: cDNA ( i x ) FEATURE:
( A ) NAME/KEY: CDS
( B ) LOCATION: 122..3617

( i x ) FEATURE:
( A ) NAME/KEY: mat_peptide
( B ) LOCATION: 173..3617

( x i ) SEQUENCE DESCRIPTION: SEQ ID NO:1:

```
GGGCGTGGAG GAGGACTGTA TCTCTGGATG CCTGGGGCCT GGTTTCAGGG CCTGATTTAT     60

TCCTCTTCCT GGGAGCTCAC TCAGGAAAGG TCCTTTCTGG GGATCACCCC ATTGGCTGAA    120

G ATG AGA CCA TTC TTC CTC TTG TGT TTT GCC CTG CCT GGC CTC CTG        166
  Met Arg Pro Phe Phe Leu Leu Cys Phe Ala Leu Pro Gly Leu Leu
  -17     -15                 -10                 -5

CAT GCC CAA CAA GCC TGC TCC CGT GGG GCC TGC TAT CCA CCT GTT GGG      214
His Ala Gln Gln Ala Cys Ser Arg Gly Ala Cys Tyr Pro Pro Val Gly
```

-continued

| | 1 | | | | 5 | | | | | 10 | | | | | |
|---|---|---|---|---|---|---|---|---|---|---|---|---|---|---|---|
| GAC | CTG | CTT | GTT | GGG | AGG | ACC | CGG | TTT | CTC | CGA | GCT | TCA | TCT | ACC | TGT | 262 |
| Asp | Leu | Leu | Val | Gly | Arg | Thr | Arg | Phe | Leu | Arg | Ala | Ser | Ser | Thr | Cys |
| 15 | | | | 20 | | | | | 25 | | | | | 30 | |
| GGA | CTG | ACC | AAG | CCT | GAG | ACC | TAC | TGC | ACC | CAG | TAT | GGC | GAG | TGG | CAG | 310 |
| Gly | Leu | Thr | Lys | Pro | Glu | Thr | Tyr | Cys | Thr | Gln | Tyr | Gly | Glu | Trp | Gln |
| | | | | 35 | | | | 40 | | | | | 45 | | |
| ATG | AAA | TGC | TGC | AAG | TGT | GAC | TCC | AGG | CAG | CCT | CAC | AAC | TAC | TAC | AGT | 358 |
| Met | Lys | Cys | Cys | Lys | Cys | Asp | Ser | Arg | Gln | Pro | His | Asn | Tyr | Tyr | Ser |
| | | | 50 | | | | | 55 | | | | | 60 | | |
| CAC | CGA | GTA | GAG | AAT | GTG | GCT | TCA | TCC | TCC | GGC | CCC | ATG | CGC | TGG | TGG | 406 |
| His | Arg | Val | Glu | Asn | Val | Ala | Ser | Ser | Ser | Gly | Pro | Met | Arg | Trp | Trp |
| | | 65 | | | | | 70 | | | | | 75 | | | |
| CAG | TCC | CAG | AAT | GAT | GTG | AAC | CCT | GTC | TCT | CTG | CAG | CTG | GAC | CTG | GAC | 454 |
| Gln | Ser | Gln | Asn | Asp | Val | Asn | Pro | Val | Ser | Leu | Gln | Leu | Asp | Leu | Asp |
| | 80 | | | | 85 | | | | | 90 | | | | | |
| AGG | AGA | TTC | CAG | CTT | CAA | GAA | GTC | ATG | ATG | GAG | TTC | CCA | GGG | GCC | CAT | 502 |
| Arg | Arg | Phe | Gln | Leu | Gln | Glu | Val | Met | Met | Glu | Phe | Pro | Gly | Ala | His |
| 95 | | | | | 100 | | | | | 105 | | | | | 110 |
| GCT | GCC | GGC | ATG | CTG | ATT | GAG | CGC | TCC | TCA | GAC | TTC | GGT | AAG | ACC | TGG | 550 |
| Ala | Ala | Gly | Met | Leu | Ile | Glu | Arg | Ser | Ser | Asp | Phe | Gly | Lys | Thr | Trp |
| | | | | 115 | | | | 120 | | | | | 125 | | |
| CGA | GTG | TAC | CAG | TAC | CTG | GCT | GCC | GAC | TGC | ACC | TCC | ACC | TTC | CCT | CGG | 598 |
| Arg | Val | Tyr | Gln | Tyr | Leu | Ala | Ala | Asp | Cys | Thr | Ser | Thr | Phe | Pro | Arg |
| | | | 130 | | | | 135 | | | | | 140 | | | |
| GTC | CGC | CAG | GGT | CGG | CCT | CAG | AGC | TGG | CAG | GAT | GTT | CGG | TGC | CAG | TCC | 646 |
| Val | Arg | Gln | Gly | Arg | Pro | Gln | Ser | Trp | Gln | Asp | Val | Arg | Cys | Gln | Ser |
| | | 145 | | | | | 150 | | | | | 155 | | | |
| CTG | CCT | CAG | AGG | CCT | AAT | GCA | CGC | CTA | AAT | GGG | GGG | AAG | GTC | CAA | CTT | 694 |
| Leu | Pro | Gln | Arg | Pro | Asn | Ala | Arg | Leu | Asn | Gly | Gly | Lys | Val | Gln | Leu |
| | 160 | | | | 165 | | | | | 170 | | | | | |
| AAC | CTT | ATG | GAT | TTA | GTG | TCT | GGG | ATT | CCA | GCA | ACT | CAA | AGT | CAA | AAA | 742 |
| Asn | Leu | Met | Asp | Leu | Val | Ser | Gly | Ile | Pro | Ala | Thr | Gln | Ser | Gln | Lys |
| 175 | | | | | 180 | | | | | 185 | | | | | 190 |
| ATT | CAA | GAG | GTG | GGG | GAG | ATC | ACA | AAC | TTG | AGA | GTC | AAT | TTC | ACC | AGG | 790 |
| Ile | Gln | Glu | Val | Gly | Glu | Ile | Thr | Asn | Leu | Arg | Val | Asn | Phe | Thr | Arg |
| | | | | 195 | | | | 200 | | | | | 205 | | |
| CTG | GCC | CCT | GTG | CCC | AAA | CTG | GAC | CAC | CCT | CCC | AGC | GCC | TAC | TAT | GCT | 838 |
| Leu | Ala | Pro | Val | Pro | Lys | Leu | Asp | His | Pro | Pro | Ser | Ala | Tyr | Tyr | Ala |
| | | | 210 | | | | 215 | | | | | 220 | | | |
| GTG | TCC | CAG | CTC | CGT | CTG | CAG | GGG | AGC | TGC | TTC | TGT | CAC | GGC | CAT | GCT | 886 |
| Val | Ser | Gln | Leu | Arg | Leu | Gln | Gly | Ser | Cys | Phe | Cys | His | Gly | His | Ala |
| | | 225 | | | | | 230 | | | | | 235 | | | |
| GAT | CGC | TGC | GCA | CCC | AAG | CCT | GGG | GCC | TCT | GCA | GGC | TCC | ACC | GCT | GTG | 934 |
| Asp | Arg | Cys | Ala | Pro | Lys | Pro | Gly | Ala | Ser | Ala | Gly | Ser | Thr | Ala | Val |
| | 240 | | | | 245 | | | | | 250 | | | | | |
| CAG | GTC | CAC | GAT | GTC | TGC | GTC | TGC | CAG | CAC | AAC | ACT | GCC | GGC | CCA | AAT | 982 |
| Gln | Val | His | Asp | Val | Cys | Val | Cys | Gln | His | Asn | Thr | Ala | Gly | Pro | Asn |
| 255 | | | | | 260 | | | | | 265 | | | | | 270 |
| TGT | GAG | CGC | TGT | GCA | CCC | TTC | TAC | AAC | AAC | CGG | CCC | TGG | AGA | CCG | GCG | 1030 |
| Cys | Glu | Arg | Cys | Ala | Pro | Phe | Tyr | Asn | Asn | Arg | Pro | Trp | Arg | Pro | Ala |
| | | | | 275 | | | | 280 | | | | | 285 | | |
| GAG | GGC | CAG | GAC | GCC | CAT | GAA | TGC | CAA | AGG | TGC | GAC | TGC | AAT | GGG | CAC | 1078 |
| Glu | Gly | Gln | Asp | Ala | His | Glu | Cys | Gln | Arg | Cys | Asp | Cys | Asn | Gly | His |
| | | | 290 | | | | 295 | | | | | 300 | | | |
| TCA | GAG | AAC | TGT | CAC | TTT | GAC | CCC | GCT | GTG | TTT | GCC | GCC | AGC | CAG | GGG | 1126 |
| Ser | Glu | Asn | Cys | His | Phe | Asp | Pro | Ala | Val | Phe | Ala | Ala | Ser | Gln | Gly |
| | | 305 | | | | | 310 | | | | | 315 | | | |
| GCA | TAT | GGA | GGT | GTG | TGT | GAC | AAT | TGC | CGG | GAC | CAC | ACC | GAA | GGC | AAG | 1174 |
| Ala | Tyr | Gly | Gly | Val | Cys | Asp | Asn | Cys | Arg | Asp | His | Thr | Glu | Gly | Lys |

|     |     |     |     |     |     | 320 |     |     |     |     | 325 |     |     |     |     | 330 |     |     |     |      |
|-----|-----|-----|-----|-----|-----|-----|-----|-----|-----|-----|-----|-----|-----|-----|-----|-----|-----|-----|-----|------|

| AAC | TGT | GAG | CGG | TGT | CAG | CTG | CAC | TAT | TTC | CGG | AAC | CGG | CGC | CCG | GGA | 1222 |
|-----|-----|-----|-----|-----|-----|-----|-----|-----|-----|-----|-----|-----|-----|-----|-----|------|
| Asn | Cys | Glu | Arg | Cys | Gln | Leu | His | Tyr | Phe | Arg | Asn | Arg | Arg | Pro | Gly |      |
| 335 |     |     |     | 340 |     |     |     |     | 345 |     |     |     |     |     | 350 |      |

| GCT | TCC | ATT | CAG | GAG | ACC | TGC | ATC | TCC | TGC | GAG | TGT | GAT | CCG | GAT | GGG | 1270 |
| Ala | Ser | Ile | Gln | Glu | Thr | Cys | Ile | Ser | Cys | Glu | Cys | Asp | Pro | Asp | Gly |      |
|     |     |     |     |     | 355 |     |     |     | 360 |     |     |     |     | 365 |     |      |

| CAG | TGG | GCA | GGG | GCT | CCC | TGT | GAC | CCA | GTG | ACC | GGG | CAG | TGT | GTG | TGC | 1318 |
| Gln | Trp | Ala | Gly | Ala | Pro | Cys | Asp | Pro | Val | Thr | Gly | Gln | Cys | Val | Cys |      |
|     |     | 370 |     |     |     |     | 375 |     |     |     |     |     | 380 |     |     |      |

| AAG | GAG | CAT | GTG | CAG | GGA | GAG | CGC | TGT | GAC | CTA | TGC | AAG | CCG | GGC | TTC | 1366 |
| Lys | Glu | His | Val | Gln | Gly | Glu | Arg | Cys | Asp | Leu | Cys | Lys | Pro | Gly | Phe |      |
|     |     | 385 |     |     |     | 390 |     |     |     |     |     | 395 |     |     |     |      |

| ACT | GGA | CTC | ACC | TAC | GCC | AAC | CCG | CAG | GGC | TGC | CAC | CGC | TGT | GAC | TGC | 1414 |
| Thr | Gly | Leu | Thr | Tyr | Ala | Asn | Pro | Gln | Gly | Cys | His | Arg | Cys | Asp | Cys |      |
|     | 400 |     |     |     |     | 405 |     |     |     |     | 410 |     |     |     |     |      |

| AAC | ATC | CTG | CCC | TCC | CGG | AGA | CTG | CCG | TGT | GAC | GAG | GAG | AGT | GGG | CGC | 1462 |
| Asn | Ile | Leu | Pro | Ser | Arg | Arg | Leu | Pro | Cys | Asp | Glu | Glu | Ser | Gly | Arg |      |
| 415 |     |     |     |     |     | 420 |     |     |     | 425 |     |     |     |     | 430 |      |

| TGC | CTT | TGT | CTG | CCC | AAC | GTA | GGT | GGT | CCC | AAA | TGT | GAC | CAG | TGT | GCT | 1510 |
| Cys | Leu | Cys | Leu | Pro | Asn | Val | Gly | Gly | Pro | Lys | Cys | Asp | Gln | Cys | Ala |      |
|     |     |     |     | 435 |     |     |     |     | 440 |     |     |     |     | 445 |     |      |

| CCC | TAC | CAC | TGG | AAG | CTG | GCC | AGT | GGC | CAG | GGC | TGT | GAA | CCG | TGT | GCC | 1558 |
| Pro | Tyr | His | Trp | Lys | Leu | Ala | Ser | Gly | Gln | Gly | Cys | Glu | Pro | Cys | Ala |      |
|     |     |     | 450 |     |     |     |     | 455 |     |     |     | 460 |     |     |     |      |

| TGC | GAC | CCG | CAC | AAC | TCC | CTC | AGC | CCA | CAG | TGC | AAC | CAG | TTC | ACA | GGG | 1606 |
| Cys | Asp | Pro | His | Asn | Ser | Leu | Ser | Pro | Gln | Cys | Asn | Gln | Phe | Thr | Gly |      |
|     |     | 465 |     |     |     |     | 470 |     |     |     |     | 475 |     |     |     |      |

| CAG | TGC | CCC | TGT | CGG | GAA | GGC | TTT | GGT | GGC | CTG | ATG | TGC | AGC | GCT | GCA | 1654 |
| Gln | Cys | Pro | Cys | Arg | Glu | Gly | Phe | Gly | Gly | Leu | Met | Cys | Ser | Ala | Ala |      |
|     | 480 |     |     |     |     | 485 |     |     |     |     | 490 |     |     |     |     |      |

| GCC | ATC | CGC | CAG | TGT | CCA | GAC | CGG | ACC | TAT | GGA | GAC | GTG | GCC | ACA | GGA | 1702 |
| Ala | Ile | Arg | Gln | Cys | Pro | Asp | Arg | Thr | Tyr | Gly | Asp | Val | Ala | Thr | Gly |      |
| 495 |     |     |     | 500 |     |     |     |     | 505 |     |     |     |     |     | 510 |      |

| TGC | CGA | GCC | TGT | GAC | TGT | GAT | TTC | CGG | GGA | ACA | GAG | GGC | CCG | GGC | TGC | 1750 |
| Cys | Arg | Ala | Cys | Asp | Cys | Asp | Phe | Arg | Gly | Thr | Glu | Gly | Pro | Gly | Cys |      |
|     |     |     |     | 515 |     |     |     |     | 520 |     |     |     |     | 525 |     |      |

| GAC | AAG | GCA | TCA | GGC | GTG | CTC | TGC | CGC | CCT | GGC | TTG | ACC | GGG | CCC | CGC | 1798 |
| Asp | Lys | Ala | Ser | Gly | Val | Leu | Cys | Arg | Pro | Gly | Leu | Thr | Gly | Pro | Arg |      |
|     |     |     | 530 |     |     |     |     | 535 |     |     |     |     | 540 |     |     |      |

| TGT | GAC | CAG | TGC | CAG | CGA | GGC | TAC | TGC | AAT | CGC | TAC | CCG | GTG | TGC | GTG | 1846 |
| Cys | Asp | Gln | Cys | Gln | Arg | Gly | Tyr | Cys | Asn | Arg | Tyr | Pro | Val | Cys | Val |      |
|     |     | 545 |     |     |     |     | 550 |     |     |     |     | 555 |     |     |     |      |

| GCC | TGC | CAC | CCT | TGC | TTC | CAG | ACC | TAT | GAT | GCG | GAC | CTC | CGG | GAG | CAG | 1894 |
| Ala | Cys | His | Pro | Cys | Phe | Gln | Thr | Tyr | Asp | Ala | Asp | Leu | Arg | Glu | Gln |      |
|     | 560 |     |     |     |     | 565 |     |     |     |     | 570 |     |     |     |     |      |

| GCC | CTG | CGC | TTT | GGT | AGA | CTC | CCG | AAT | GCC | ACC | GCC | AGC | CTG | TGG | TCA | 1942 |
| Ala | Leu | Arg | Phe | Gly | Arg | Leu | Pro | Asn | Ala | Thr | Ala | Ser | Leu | Trp | Ser |      |
| 575 |     |     |     |     | 580 |     |     |     |     | 585 |     |     |     |     | 590 |      |

| GGG | CCT | GGG | CTG | GAG | GAC | CGT | GGC | CTG | GCC | TCC | CGG | ATC | CTA | GAT | GCA | 1990 |
| Gly | Pro | Gly | Leu | Glu | Asp | Arg | Gly | Leu | Ala | Ser | Arg | Ile | Leu | Asp | Ala |      |
|     |     |     |     | 595 |     |     |     |     | 600 |     |     |     |     | 605 |     |      |

| AAG | AGT | AAG | ATT | GAG | CAG | ATC | CGA | GCA | GTT | CTC | AGC | AGC | CCC | GCA | GTC | 2038 |
| Lys | Ser | Lys | Ile | Glu | Gln | Ile | Arg | Ala | Val | Leu | Ser | Ser | Pro | Ala | Val |      |
|     |     |     | 610 |     |     |     |     | 615 |     |     |     |     | 620 |     |     |      |

| ACA | GAG | CAG | GAG | GTG | GCT | CAG | GTG | GCC | AGT | GCC | ATC | CTC | TCC | CTC | AGG | 2086 |
| Thr | Glu | Gln | Glu | Val | Ala | Gln | Val | Ala | Ser | Ala | Ile | Leu | Ser | Leu | Arg |      |
|     |     | 625 |     |     |     |     | 630 |     |     |     |     | 635 |     |     |     |      |

| CGA | ACT | CTC | CAG | GGC | CTG | CAG | CTG | GAT | CTG | CCC | CTG | GAG | GAG | GAG | ACG | 2134 |
| Arg | Thr | Leu | Gln | Gly | Leu | Gln | Leu | Asp | Leu | Pro | Leu | Glu | Glu | Glu | Thr |      |

```
                        640                           645                           650
TTG  TCC  CTT  CCG  AGA  GAC  CTG  GAG  AGT  CTT  GAC  AGA  AGC  TTC  AAT  GGT          2182
Leu  Ser  Leu  Pro  Arg  Asp  Leu  Glu  Ser  Leu  Asp  Arg  Ser  Phe  Asn  Gly
655                 660                      665                      670

CTC  CTT  ACT  ATG  TAT  CAG  AGG  AAG  AGG  GAG  CAG  TTT  GAA  AAA  ATA  AGC          2230
Leu  Leu  Thr  Met  Tyr  Gln  Arg  Lys  Arg  Glu  Gln  Phe  Glu  Lys  Ile  Ser
                    675                      680                      685

AGT  GCT  GAT  CCT  TCA  GGA  GCC  TTC  CGG  ATG  CTG  AGC  ACA  GCC  TAC  GAG          2278
Ser  Ala  Asp  Pro  Ser  Gly  Ala  Phe  Arg  Met  Leu  Ser  Thr  Ala  Tyr  Glu
               690                      695                      700

CAG  TCA  GCC  CAG  GCT  GCT  CAG  CAG  GTC  TCC  GAC  AGC  TCG  CGC  CTT  TTG          2326
Gln  Ser  Ala  Gln  Ala  Ala  Gln  Gln  Val  Ser  Asp  Ser  Ser  Arg  Leu  Leu
          705                      710                      715

GAC  CAG  CTC  AGG  GAC  AGC  CGG  AGA  GAG  GCA  GAG  AGG  CTG  GTG  CGG  CAG          2374
Asp  Gln  Leu  Arg  Asp  Ser  Arg  Arg  Glu  Ala  Glu  Arg  Leu  Val  Arg  Gln
     720                      725                      730

GCG  GGA  GGA  GGA  GGA  GGC  ACC  GGC  AGC  CCC  AAG  CTT  GTG  GCC  CTG  AGG          2422
Ala  Gly  Gly  Gly  Gly  Gly  Thr  Gly  Ser  Pro  Lys  Leu  Val  Ala  Leu  Arg
735                      740                      745                      750

TTG  GAG  ATG  TCT  TCG  TTG  CCT  GAC  CTG  ACA  CCC  ACC  TTC  AAC  AAG  CTC          2470
Leu  Glu  Met  Ser  Ser  Leu  Pro  Asp  Leu  Thr  Pro  Thr  Phe  Asn  Lys  Leu
                    755                      760                      765

TGT  GGC  AAC  TCC  AGG  CAG  ATG  GCT  TGC  ACC  CCA  ATA  TCA  TGC  CCT  GGT          2518
Cys  Gly  Asn  Ser  Arg  Gln  Met  Ala  Cys  Thr  Pro  Ile  Ser  Cys  Pro  Gly
               770                      775                      780

GAG  CTA  TGT  CCC  CAA  GAC  AAT  GGC  ACA  GCC  TGT  GCG  TCC  CGC  TGC  AGG          2566
Glu  Leu  Cys  Pro  Gln  Asp  Asn  Gly  Thr  Ala  Cys  Ala  Ser  Arg  Cys  Arg
          785                      790                      795

GGT  GTC  CTT  CCC  AGG  GCC  GGT  GGG  GCC  TTC  TTG  ATG  GCG  GGG  CAG  GTG          2614
Gly  Val  Leu  Pro  Arg  Ala  Gly  Gly  Ala  Phe  Leu  Met  Ala  Gly  Gln  Val
     800                      805                      810

GCT  GAG  CAG  CTG  CGG  GCT  TCA  ATG  CCA  GCT  CCA  GCG  ACC  AGG  CAG  ATG          2662
Ala  Glu  Gln  Leu  Arg  Ala  Ser  Met  Pro  Ala  Pro  Ala  Thr  Arg  Gln  Met
815                      820                      825                      830

ATT  AGG  GCA  GCC  GAG  GAA  TCT  GCC  TCA  CAG  ATT  CAA  TCC  AGT  GCC  CAG          2710
Ile  Arg  Ala  Ala  Glu  Glu  Ser  Ala  Ser  Gln  Ile  Gln  Ser  Ser  Ala  Gln
                    835                      840                      845

CGC  TTG  GAG  ACC  CAG  GTG  AGC  GCC  AGC  CGC  TCC  CAG  ATG  GAG  GAA  GAT          2758
Arg  Leu  Glu  Thr  Gln  Val  Ser  Ala  Ser  Arg  Ser  Gln  Met  Glu  Glu  Asp
               850                      855                      860

GTC  AGA  CGC  ACA  CGG  CTC  CTA  ATC  CAG  CAG  GTC  CGG  GAC  TTC  CTA  ACA          2806
Val  Arg  Arg  Thr  Arg  Leu  Leu  Ile  Gln  Gln  Val  Arg  Asp  Phe  Leu  Thr
          865                      870                      875

GAC  CCC  GAC  ACT  GAT  GCA  GCC  ACT  ATC  CAG  GAG  GTC  AGG  CGA  GCC  GTG          2854
Asp  Pro  Asp  Thr  Asp  Ala  Ala  Thr  Ile  Gln  Glu  Val  Arg  Arg  Ala  Val
     880                      885                      890

CTG  GCC  CTG  TGG  CTG  CCC  ACA  GAC  TCA  GCT  ACT  GTT  CTG  CAG  AAG  ATG          2902
Leu  Ala  Leu  Trp  Leu  Pro  Thr  Asp  Ser  Ala  Thr  Val  Leu  Gln  Lys  Met
895                      900                      905                      910

AAT  GAG  ATC  CAG  GCC  ATT  GCA  GCC  AGG  CTC  CCC  AAC  GTG  GAC  TTG  GTG          2950
Asn  Glu  Ile  Gln  Ala  Ile  Ala  Ala  Arg  Leu  Pro  Asn  Val  Asp  Leu  Val
                    915                      920                      925

CTG  TCC  CAG  ACC  AAG  CAG  GAC  ATT  GGC  GGT  GCC  CGC  CGG  TTG  CAG  GCT          2998
Leu  Ser  Gln  Thr  Lys  Gln  Asp  Ile  Gly  Gly  Ala  Arg  Arg  Leu  Gln  Ala
               930                      935                      940

GAG  GCT  GAG  GAA  GCC  AGG  AGC  CGA  GCC  CAT  GCA  GTG  GAG  GGC  CAG  GTG          3046
Glu  Ala  Glu  Glu  Ala  Arg  Ser  Arg  Ala  His  Ala  Val  Glu  Gly  Gln  Val
          945                      950                      955

GAG  GAT  GTG  GTT  GGG  AAC  CTG  CGG  CAG  GGA  ACA  GTG  GCA  CTG  CAG  GAA          3094
Glu  Asp  Val  Val  Gly  Asn  Leu  Arg  Gln  Gly  Thr  Val  Ala  Leu  Gln  Glu
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     | 960 |     |     |     |     | 965 |     |     |     |     |     | 970 |     |     |      |
| GCT | CAG | GAC | ACC | ATG | CAA | GGC | ACC | AGC | CGG | TCC | CTT | CGG | CTT | ATC | CAG | 3142 |
| Ala | Gln | Asp | Thr | Met | Gln | Gly | Thr | Ser | Arg | Ser | Leu | Arg | Leu | Ile | Gln |      |
| 975 |     |     |     | 980 |     |     |     |     | 985 |     |     |     |     |     | 990 |      |
| GAC | AGG | GTT | GCT | GAG | GTT | CAG | CAG | GTA | CTC | GGC | CAG | CAA | AAG | CTG | GTG | 3190 |
| Asp | Arg | Val | Ala | Glu | Val | Gln | Gln | Val | Leu | Gly | Gln | Gln | Lys | Leu | Val |      |
|     |     |     |     | 995 |     |     |     |     | 1000|     |     |     |     | 1005|     |      |
| ACA | AGC | ATG | ACC | AAG | CAG | CTG | GGT | GAC | TTC | TGG | ACA | CGG | ATG | GAG | GAG | 3238 |
| Thr | Ser | Met | Thr | Lys | Gln | Leu | Gly | Asp | Phe | Trp | Thr | Arg | Met | Glu | Glu |      |
|     |     |     | 1010|     |     |     |     | 1015|     |     |     |     | 1020|     |     |      |
| CTC | CGC | CAC | CAA | GCC | CGG | CAG | CAG | GGG | GCA | GAG | GCA | GTC | CAG | GCC | CAG | 3286 |
| Leu | Arg | His | Gln | Ala | Arg | Gln | Gln | Gly | Ala | Glu | Ala | Val | Gln | Ala | Gln |      |
|     |     | 1025|     |     |     |     | 1030|     |     |     |     | 1035|     |     |     |      |
| CAG | CTT | GCG | GAA | GGT | GCC | AGC | GAG | CAG | GCA | TTG | AGT | GCC | CAA | GAG | GGA | 3334 |
| Gln | Leu | Ala | Glu | Gly | Ala | Ser | Glu | Gln | Ala | Leu | Ser | Ala | Gln | Glu | Gly |      |
|     | 1040|     |     |     |     | 1045|     |     |     |     | 1050|     |     |     |     |      |
| TTT | GAG | AGA | ATA | AAA | CAA | AAG | TAT | GCT | GAG | TTG | AAG | GAC | CGG | TTG | GGT | 3382 |
| Phe | Glu | Arg | Ile | Lys | Gln | Lys | Tyr | Ala | Glu | Leu | Lys | Asp | Arg | Leu | Gly |      |
| 1055|     |     |     |     | 1060|     |     |     |     | 1065|     |     |     |     | 1070|      |
| CAG | AGT | TCC | ATG | CTG | GGT | GAG | CAG | GGT | GCC | CGG | ATC | CAG | AGT | GTG | AAG | 3430 |
| Gln | Ser | Ser | Met | Leu | Gly | Glu | Gln | Gly | Ala | Arg | Ile | Gln | Ser | Val | Lys |      |
|     |     |     |     | 1075|     |     |     |     | 1080|     |     |     |     | 1085|     |      |
| ACA | GAG | GCA | GAG | GAG | CTG | TTT | GGG | GAG | ACC | ATG | GAG | ATG | ATG | GAC | AGG | 3478 |
| Thr | Glu | Ala | Glu | Glu | Leu | Phe | Gly | Glu | Thr | Met | Glu | Met | Met | Asp | Arg |      |
|     |     |     | 1090|     |     |     |     | 1095|     |     |     |     | 1100|     |     |      |
| ATG | AAA | GAC | ATG | GAG | TTG | GAG | CTG | CTG | CGG | GCA | GCA | GGC | CAT | CAT | GCT | 3526 |
| Met | Lys | Asp | Met | Glu | Leu | Glu | Leu | Leu | Arg | Ala | Ala | Gly | His | His | Ala |      |
|     |     |     | 1105|     |     |     |     | 1110|     |     |     |     | 1115|     |     |      |
| GCG | CTC | AGC | GAC | CTG | ACA | GGA | CTG | GAG | AAG | CGT | GTG | GAG | CAG | ATC | CGT | 3574 |
| Ala | Leu | Ser | Asp | Leu | Thr | Gly | Leu | Glu | Lys | Arg | Val | Glu | Gln | Ile | Arg |      |
|     |     | 1120|     |     |     |     | 1125|     |     |     |     | 1130|     |     |     |      |
| GAC | CAC | ATC | AAT | GGG | CGC | GTG | CTC | TAC | TAT | GCC | ACC | TGC | AAG | T   |     | 3617 |
| Asp | His | Ile | Asn | Gly | Arg | Val | Leu | Tyr | Tyr | Ala | Thr | Cys | Lys |     |     |      |
| 1135|     |     |     |     | 1140|     |     |     |     | 1145|     |     |     |     |     |      |

```
GATGCTACAC GTTCCAGCCC GTTGCCCCAC TCATCTGCGC GCTTTGCTTT TGGTTGGGGG    3677

GCAGATTGGG TTGGAATGCT TTCCATCTCC AGGAGACTTT CATGTAGCCC AAAGTACAGC    3737

CTGGACCACC CCTGGTGTGA GTAGCTAGTA AGATTACCCT GAGCTGCAGC TGAGCCTGAG    3797

CCAATGGGAC AGTTACACTT GACAGACAAA GATGGTGGAG ATTGGCATGC CATTGAAACT    3857

AAGAGCTCTC AAGTCAAGGA AGCTGGGCTG GGCAGTATCC CCCGCCTTTA GTTCTCCACA    3917

AAAAAAAAAA AAAA                                                      3931
```

( 2 ) INFORMATION FOR SEQ ID NO:2:

( i ) SEQUENCE CHARACTERISTICS:
        ( A ) LENGTH: 1165 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Arg | Pro | Phe | Phe | Leu | Leu | Cys | Phe | Ala | Leu | Pro | Gly | Leu | Leu | His |
| --- | --- | --- | --- | --- | --- | --- | --- | --- | --- | --- | --- | --- | --- | --- | --- |
| -17 |     | -15 |     |     |     |     | -10 |     |     |     |     | -5  |     |     |     |

| Ala | Gln | Gln | Ala | Cys | Ser | Arg | Gly | Ala | Cys | Tyr | Pro | Pro | Val | Gly | Asp |
| --- | --- | --- | --- | --- | --- | --- | --- | --- | --- | --- | --- | --- | --- | --- | --- |
|     | 1   |     |     |     | 5   |     |     |     |     | 10  |     |     |     |     | 15  |

| Leu | Leu | Val | Gly | Arg | Thr | Arg | Phe | Leu | Arg | Ala | Ser | Ser | Thr | Cys | Gly |
| --- | --- | --- | --- | --- | --- | --- | --- | --- | --- | --- | --- | --- | --- | --- | --- |
|     |     |     |     |     | 20  |     |     |     | 25  |     |     |     |     | 30  |     |

| Leu | Thr | Lys | Pro | Glu | Thr | Tyr | Cys | Thr | Gln | Tyr | Gly | Glu | Trp | Gln | Met |
| --- | --- | --- | --- | --- | --- | --- | --- | --- | --- | --- | --- | --- | --- | --- | --- |

|  | 35 |  |  |  | 40 |  |  |  | 45 |  |  |
|---|---|---|---|---|---|---|---|---|---|---|---|
| Lys | Cys | Cys<br>50 | Lys | Cys | Asp | Ser<br>55 | Arg | Gln | Pro | His | Asn<br>60 | Tyr | Tyr | Ser | His |

Arg Val Glu Asn Val Ala Ser Ser Ser Gly Pro Met Arg Trp Trp Gln
    65              70              75

Ser Gln Asn Asp Val Asn Pro Val Ser Leu Gln Leu Asp Leu Asp Arg
80              85              90                          95

Arg Phe Gln Leu Gln Glu Val Met Met Glu Phe Pro Gly Ala His Ala
            100             105                     110

Ala Gly Met Leu Ile Glu Arg Ser Ser Asp Phe Gly Lys Thr Trp Arg
            115             120                     125

Val Tyr Gln Tyr Leu Ala Ala Asp Cys Thr Ser Thr Phe Pro Arg Val
        130             135                 140

Arg Gln Gly Arg Pro Gln Ser Trp Gln Asp Val Arg Cys Gln Ser Leu
    145             150                 155

Pro Gln Arg Pro Asn Ala Arg Leu Asn Gly Gly Lys Val Gln Leu Asn
160             165                 170                     175

Leu Met Asp Leu Val Ser Gly Ile Pro Ala Thr Gln Ser Gln Lys Ile
            180             185                     190

Gln Glu Val Gly Glu Ile Thr Asn Leu Arg Val Asn Phe Thr Arg Leu
            195             200                 205

Ala Pro Val Pro Lys Leu Asp His Pro Pro Ser Ala Tyr Tyr Ala Val
        210             215                 220

Ser Gln Leu Arg Leu Gln Gly Ser Cys Phe Cys His Gly His Ala Asp
    225             230             235

Arg Cys Ala Pro Lys Pro Gly Ala Ser Ala Gly Ser Thr Ala Val Gln
240             245             250                         255

Val His Asp Val Cys Val Cys Gln His Asn Thr Ala Gly Pro Asn Cys
            260             265                 270

Glu Arg Cys Ala Pro Phe Tyr Asn Asn Arg Pro Trp Arg Pro Ala Glu
            275             280                 285

Gly Gln Asp Ala His Glu Cys Gln Arg Cys Asp Cys Asn Gly His Ser
        290             295                 300

Glu Asn Cys His Phe Asp Pro Ala Val Phe Ala Ala Ser Gln Gly Ala
    305             310                 315

Tyr Gly Gly Val Cys Asp Asn Cys Arg Asp His Thr Glu Gly Lys Asn
320             325                 330                     335

Cys Glu Arg Cys Gln Leu His Tyr Phe Arg Asn Arg Arg Pro Gly Ala
            340             345                 350

Ser Ile Gln Glu Thr Cys Ile Ser Cys Glu Cys Asp Pro Asp Gly Gln
            355             360                 365

Trp Ala Gly Ala Pro Cys Asp Pro Val Thr Gly Gln Cys Val Cys Lys
        370             375                 380

Glu His Val Gln Gly Glu Arg Cys Asp Leu Cys Lys Pro Gly Phe Thr
    385             390                 395

Gly Leu Thr Tyr Ala Asn Pro Gln Gly Cys His Arg Cys Asp Cys Asn
400             405                 410                     415

Ile Leu Pro Ser Arg Arg Leu Pro Cys Asp Glu Ser Gly Arg Cys
            420             425                 430

Leu Cys Leu Pro Asn Val Gly Gly Pro Lys Cys Asp Gln Cys Ala Pro
            435             440                 445

Tyr His Trp Lys Leu Ala Ser Gly Gln Gly Cys Glu Pro Cys Ala Cys
        450             455                 460

-continued

| | | | | | | | | | | | | | | |
|---|---|---|---|---|---|---|---|---|---|---|---|---|---|---|
| Asp | Pro | His | Asn | Ser | Leu | Ser | Pro | Gln | Cys | Asn | Gln | Phe | Thr | Gly | Gln |
| | 465 | | | | 470 | | | | 475 | | | | | |
| Cys | Pro | Cys | Arg | Glu | Gly | Phe | Gly | Gly | Leu | Met | Cys | Ser | Ala | Ala | Ala |
| 480 | | | | 485 | | | | | 490 | | | | | 495 |
| Ile | Arg | Gln | Cys | Pro | Asp | Arg | Thr | Tyr | Gly | Asp | Val | Ala | Thr | Gly | Cys |
| | | | | 500 | | | | 505 | | | | | 510 | |
| Arg | Ala | Cys | Asp | Cys | Asp | Phe | Arg | Gly | Thr | Glu | Gly | Pro | Gly | Cys | Asp |
| | | | 515 | | | | | 520 | | | | 525 | | |
| Lys | Ala | Ser | Gly | Val | Leu | Cys | Arg | Pro | Gly | Leu | Thr | Gly | Pro | Arg | Cys |
| | | 530 | | | | | 535 | | | | 540 | | | |
| Asp | Gln | Cys | Gln | Arg | Gly | Tyr | Cys | Asn | Arg | Tyr | Pro | Val | Cys | Val | Ala |
| | 545 | | | | 550 | | | | 555 | | | | | |
| Cys | His | Pro | Cys | Phe | Gln | Thr | Tyr | Asp | Ala | Asp | Leu | Arg | Glu | Gln | Ala |
| 560 | | | | 565 | | | | | 570 | | | | | 575 |
| Leu | Arg | Phe | Gly | Arg | Leu | Pro | Asn | Ala | Thr | Ala | Ser | Leu | Trp | Ser | Gly |
| | | | 580 | | | | | 585 | | | | | 590 | |
| Pro | Gly | Leu | Glu | Asp | Arg | Gly | Leu | Ala | Ser | Arg | Ile | Leu | Asp | Ala | Lys |
| | | | 595 | | | | 600 | | | | | 605 | | |
| Ser | Lys | Ile | Glu | Gln | Ile | Arg | Ala | Val | Leu | Ser | Ser | Pro | Ala | Val | Thr |
| | | 610 | | | | | 615 | | | | | 620 | | |
| Glu | Gln | Glu | Val | Ala | Gln | Val | Ala | Ser | Ala | Ile | Leu | Ser | Leu | Arg | Arg |
| | 625 | | | | 630 | | | | | 635 | | | | |
| Thr | Leu | Gln | Gly | Leu | Gln | Leu | Asp | Leu | Pro | Leu | Glu | Glu | Glu | Thr | Leu |
| 640 | | | | 645 | | | | | 650 | | | | | 655 |
| Ser | Leu | Pro | Arg | Asp | Leu | Glu | Ser | Leu | Asp | Arg | Ser | Phe | Asn | Gly | Leu |
| | | | 660 | | | | | 665 | | | | | 670 | |
| Leu | Thr | Met | Tyr | Gln | Arg | Lys | Arg | Glu | Gln | Phe | Glu | Lys | Ile | Ser | Ser |
| | | | 675 | | | | | 680 | | | | | 685 | |
| Ala | Asp | Pro | Ser | Gly | Ala | Phe | Arg | Met | Leu | Ser | Thr | Ala | Tyr | Glu | Gln |
| | | 690 | | | | | 695 | | | | 700 | | | |
| Ser | Ala | Gln | Ala | Ala | Gln | Gln | Val | Ser | Asp | Ser | Ser | Arg | Leu | Leu | Asp |
| | 705 | | | | 710 | | | | | 715 | | | | |
| Gln | Leu | Arg | Asp | Ser | Arg | Arg | Glu | Ala | Glu | Arg | Leu | Val | Arg | Gln | Ala |
| 720 | | | | | 725 | | | | 730 | | | | | 735 |
| Gly | Gly | Gly | Gly | Gly | Thr | Gly | Ser | Pro | Lys | Leu | Val | Ala | Leu | Arg | Leu |
| | | | | 740 | | | | | 745 | | | | | 750 |
| Glu | Met | Ser | Ser | Leu | Pro | Asp | Leu | Thr | Pro | Thr | Phe | Asn | Lys | Leu | Cys |
| | | | 755 | | | | | 760 | | | | | 765 | |
| Gly | Asn | Ser | Arg | Gln | Met | Ala | Cys | Thr | Pro | Ile | Ser | Cys | Pro | Gly | Glu |
| | | 770 | | | | | 775 | | | | | 780 | | |
| Leu | Cys | Pro | Gln | Asp | Asn | Gly | Thr | Ala | Cys | Ala | Ser | Arg | Cys | Arg | Gly |
| | 785 | | | | | 790 | | | | | 795 | | | |
| Val | Leu | Pro | Arg | Ala | Gly | Gly | Ala | Phe | Leu | Met | Ala | Gly | Gln | Val | Ala |
| 800 | | | | | 805 | | | | | 810 | | | | | 815 |
| Glu | Gln | Leu | Arg | Ala | Ser | Met | Pro | Ala | Pro | Ala | Thr | Arg | Gln | Met | Ile |
| | | | | 820 | | | | | 825 | | | | | 830 |
| Arg | Ala | Ala | Glu | Glu | Ser | Ala | Ser | Gln | Ile | Gln | Ser | Ser | Ala | Gln | Arg |
| | | | 835 | | | | | 840 | | | | | 845 | |
| Leu | Glu | Thr | Gln | Val | Ser | Ala | Ser | Arg | Ser | Gln | Met | Glu | Glu | Asp | Val |
| | | 850 | | | | | 855 | | | | | 860 | | |
| Arg | Arg | Thr | Arg | Leu | Leu | Ile | Gln | Gln | Val | Arg | Asp | Phe | Leu | Thr | Asp |
| | 865 | | | | | 870 | | | | | 875 | | | | |
| Pro | Asp | Thr | Asp | Ala | Ala | Thr | Ile | Gln | Glu | Val | Arg | Arg | Ala | Val | Leu |
| 880 | | | | | 885 | | | | | 890 | | | | | 895 |

| | | | | | | | | | | | | | | |
|---|---|---|---|---|---|---|---|---|---|---|---|---|---|---|
|Ala|Leu|Trp|Leu|Pro<br>900|Thr|Asp|Ser|Ala|Thr<br>905|Val|Leu|Gln|Lys|Met<br>910|Asn|
|Glu|Ile|Gln|Ala<br>915|Ile|Ala|Ala|Arg|Leu<br>920|Pro|Asn|Val|Asp|Leu<br>925|Val|Leu|
|Ser|Gln|Thr<br>930|Lys|Gln|Asp|Ile|Gly<br>935|Gly|Ala|Arg|Arg|Leu<br>940|Gln|Ala|Glu|
|Ala|Glu<br>945|Gly|Ala|Arg|Ser|Arg<br>950|Ala|His|Ala|Val|Glu<br>955|Gly|Gln|Val|Glu|
|Asp<br>960|Val|Val|Gly|Asn|Leu<br>965|Arg|Gln|Gly|Thr|Val<br>970|Ala|Leu|Gln|Glu|Ala<br>975|
|Gln|Asp|Thr|Met|Gln<br>980|Gly|Thr|Ser|Arg|Ser<br>985|Leu|Arg|Leu|Ile|Gln<br>990|Asp|
|Arg|Val|Ala|Glu<br>995|Val|Gln|Gln|Val|Leu<br>1000|Gly|Gln|Gln|Lys|Leu<br>1005|Val|Thr|
|Ser|Met|Thr|Lys<br>1010|Gln|Leu|Gly|Asp|Phe<br>1015|Trp|Thr|Arg|Met<br>1020|Glu|Glu|Leu|
|Arg|His<br>1025|Gln|Ala|Arg|Gln|Gln<br>1030|Gly|Ala|Glu|Ala|Val<br>1035|Gln|Ala|Gln|Gln|
|Leu<br>1040|Ala|Glu|Gly|Ala|Ser<br>1045|Glu|Gln|Ala|Leu|Ser<br>1050|Ala|Gln|Glu|Gly|Phe<br>1055|
|Glu|Arg|Ile|Lys|Gln<br>1060|Lys|Tyr|Ala|Glu|Leu<br>1065|Lys|Asp|Arg|Leu|Gly<br>1070|Gln|
|Ser|Ser|Met|Leu<br>1075|Gly|Glu|Gln|Gly|Ala<br>1080|Arg|Ile|Gln|Ser|Val<br>1085|Lys|Thr|
|Glu|Ala|Glu|Glu<br>1090|Leu|Phe|Gly|Glu|Thr<br>1095|Met|Glu|Met|Asp<br>1100|Arg|Met|
|Lys|Asp|Met<br>1105|Glu|Leu|Glu|Leu<br>1110|Leu|Arg|Ala|Ala|Gly<br>1115|His|His|Ala|Ala|
|Leu|Ser<br>1120|Asp|Leu|Thr|Gly|Leu<br>1125|Glu|Lys|Arg|Val|Glu<br>1130|Gln|Ile|Arg|Asp<br>1135|
|His|Ile|Asn|Gly|Arg<br>1140|Val|Leu|Tyr|Tyr|Ala<br>1145|Thr|Cys|Lys|

( 2 ) INFORMATION FOR SEQ ID NO:3:

( i ) SEQUENCE CHARACTERISTICS:
        ( A ) LENGTH: 1147 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Domain
        ( B ) LOCATION: 1..231

( i x ) FEATURE:
        ( A ) NAME/KEY: Domain
        ( B ) LOCATION: 232..411

( i x ) FEATURE:
        ( A ) NAME/KEY: Domain
        ( B ) LOCATION: 412..765

( i x ) FEATURE:
        ( A ) NAME/KEY: Domain
        ( B ) LOCATION: 766..1147

( x i ) SEQUENCE DESCRIPTION: SEQ ID NO:3:

Gln Gln Ala Cys Ser Arg Gly Ala Cys Tyr Pro Pro Val Gly Asp Leu

-continued

| 1 | | | | 5 | | | | | 10 | | | | | 15 | |
|---|---|---|---|---|---|---|---|---|---|---|---|---|---|---|---|
| Leu | Val | Gly | Arg 20 | Thr | Arg | Phe | Leu | Arg 25 | Ala | Ser | Ser | Thr 30 | Cys | Gly | Leu |
| Thr | Lys | Pro 35 | Glu | Thr | Tyr | Cys | Thr 40 | Gln | Tyr | Gly | Glu 45 | Trp | Gln | Met | Lys |
| Cys | Cys 50 | Lys | Cys | Asp | Ser 55 | Arg | Gln | Pro | His | Asn 60 | Tyr | Tyr | Ser | His | Arg |
| Val 65 | Glu | Asn | Val | Ala | Ser 70 | Ser | Ser | Gly | Pro | Met 75 | Arg | Trp | Trp | Gln | Ser 80 |
| Gln | Asn | Asp | Val | Asn 85 | Pro | Val | Ser | Leu | Gln 90 | Leu | Asp | Leu | Asp | Arg 95 | Arg |
| Phe | Gln | Leu | Gln 100 | Glu | Val | Met | Met | Glu 105 | Phe | Pro | Gly | Ala | His 110 | Ala | Ala |
| Gly | Met | Leu 115 | Ile | Glu | Arg | Ser | Ser 120 | Asp | Phe | Gly | Lys | Thr 125 | Trp | Arg | Val |
| Tyr | Gln 130 | Tyr | Leu | Ala | Ala | Asp 135 | Cys | Thr | Ser | Thr | Phe 140 | Pro | Arg | Val | Arg |
| Gln 145 | Gly | Arg | Pro | Gln | Ser 150 | Trp | Gln | Asp | Val | Arg 155 | Cys | Gln | Ser | Leu | Pro 160 |
| Gln | Arg | Pro | Asn | Ala 165 | Arg | Leu | Asn | Gly | Gly 170 | Lys | Val | Gln | Leu | Asn 175 | Leu |
| Met | Asp | Leu | Val 180 | Ser | Gly | Ile | Pro | Ala 185 | Thr | Gln | Ser | Gln | Lys 190 | Ile | Gln |
| Glu | Val | Gly 195 | Glu | Ile | Thr | Asn | Leu 200 | Arg | Val | Asn | Phe | Thr 205 | Arg | Leu | Ala |
| Pro | Val 210 | Pro | Lys | Leu | Asp | His 215 | Pro | Pro | Ser | Ala | Tyr 220 | Tyr | Ala | Val | Ser |
| Gln 225 | Leu | Arg | Leu | Gln | Gly 230 | Ser | Cys | Phe | Cys | His 235 | Gly | His | Ala | Asp | Arg 240 |
| Cys | Ala | Pro | Lys | Pro 245 | Gly | Ala | Ser | Ala | Gly 250 | Ser | Thr | Ala | Val | Gln 255 | Val |
| His | Asp | Val | Cys 260 | Val | Cys | Gln | His | Asn 265 | Thr | Ala | Gly | Pro | Asn 270 | Cys | Glu |
| Arg | Cys | Ala 275 | Pro | Phe | Tyr | Asn | Asn 280 | Arg | Pro | Trp | Arg | Pro 285 | Ala | Glu | Gly |
| Gln | Asp 290 | Ala | His | Glu | Cys | Gln 295 | Arg | Cys | Asp | Cys | Asn 300 | Gly | His | Ser | Glu |
| Asn 305 | Cys | His | Phe | Asp | Pro 310 | Ala | Val | Phe | Ala | Ala 315 | Ser | Gln | Gly | Ala | Tyr 320 |
| Gly | Gly | Val | Cys | Asp 325 | Asn | Cys | Arg | Asp | His 330 | Thr | Glu | Gly | Lys | Asn 335 | Cys |
| Glu | Arg | Cys | Gln 340 | Leu | His | Tyr | Phe | Arg 345 | Asn | Arg | Arg | Pro | Gly 350 | Ala | Ser |
| Ile | Gln | Glu 355 | Thr | Cys | Ile | Ser | Cys 360 | Glu | Cys | Asp | Pro | Asp 365 | Gly | Gln | Trp |
| Ala | Gly 370 | Ala | Pro | Cys | Asp | Pro 375 | Val | Thr | Gly | Gln | Cys 380 | Val | Cys | Lys | Glu |
| His 385 | Val | Gln | Gly | Glu | Arg 390 | Cys | Asp | Leu | Cys | Lys 395 | Pro | Gly | Phe | Thr | Gly 400 |
| Leu | Thr | Tyr | Ala | Asn 405 | Pro | Gln | Gly | Cys | His 410 | Arg | Cys | Asp | Cys | Asn 415 | Ile |
| Leu | Pro | Ser | Arg 420 | Arg | Leu | Pro | Cys | Asp 425 | Glu | Glu | Ser | Gly | Arg 430 | Cys | Leu |

```
Cys Leu Pro Asn Val Gly Gly Pro Lys Cys Asp Gln Cys Ala Pro Tyr
        435             440             445

His Trp Lys Leu Ala Ser Gln Gly Cys Glu Pro Cys Ala Cys Asp
    450             455             460

Pro His Asn Ser Leu Ser Pro Gln Cys Asn Gln Phe Thr Gly Gln Cys
465             470             475                         480

Pro Cys Arg Glu Gly Phe Gly Gly Leu Met Cys Ser Ala Ala Ala Ile
                485             490                     495

Arg Gln Cys Pro Asp Arg Thr Tyr Gly Asp Val Ala Thr Gly Cys Arg
                500             505             510

Ala Cys Asp Cys Asp Phe Arg Gly Thr Glu Gly Pro Gly Cys Asp Lys
        515             520             525

Ala Ser Gly Val Leu Cys Arg Pro Gly Leu Thr Gly Pro Arg Cys Asp
530             535             540

Gln Cys Arg Gly Tyr Cys Asn Arg Tyr Pro Val Cys Val Ala Cys His
545             550             555                         560

Pro Cys Phe Gln Thr Tyr Asp Ala Asp Leu Arg Glu Gln Ala Leu Arg
                565             570             575

Phe Gly Arg Leu Pro Asn Ala Thr Ala Ser Leu Trp Ser Gly Pro Gly
            580             585             590

Leu Glu Asp Arg Gly Leu Ala Ser Arg Ile Leu Asp Ala Lys Ser Lys
            595             600             605

Ile Glu Gln Ile Arg Ala Val Leu Ser Ser Pro Ala Val Thr Glu Gln
610             615             620

Glu Val Ala Gln Val Ala Ser Ala Ile Leu Ser Leu Arg Arg Thr Leu
625             630             635                         640

Gln Gly Leu Gln Leu Asp Leu Pro Leu Glu Glu Thr Leu Ser Leu
                645             650             655

Pro Arg Asp Leu Glu Ser Leu Asp Arg Ser Phe Asn Gly Leu Leu Thr
            660             665             670

Met Tyr Gln Arg Lys Arg Glu Gln Phe Glu Lys Ile Ser Ser Ala Asp
        675             680             685

Pro Ser Gly Ala Phe Arg Met Leu Ser Thr Ala Tyr Glu Gln Ser Ala
690             695             700

Gln Ala Ala Gln Gln Val Ser Asp Ser Ser Arg Leu Leu Asp Gln Leu
705             710             715                         720

Arg Asp Ser Arg Arg Glu Ala Glu Arg Leu Val Arg Gln Ala Gly Gly
                725             730             735

Gly Gly Gly Thr Gly Ser Pro Lys Leu Val Ala Leu Arg Leu Glu Met
            740             745             750

Ser Ser Leu Pro Asp Leu Thr Pro Thr Phe Asn Lys Leu Cys Gly Asn
        755             760             765

Ser Arg Gln Met Ala Cys Thr Pro Ile Ser Cys Pro Gly Glu Leu Cys
    770             775             780

Pro Gln Asp Asn Gly Thr Ala Cys Ala Ser Arg Cys Arg Gly Val Leu
785             790             795                         800

Pro Arg Ala Gly Gly Ala Phe Leu Met Ala Gly Gln Val Ala Glu Gln
                805             810             815

Leu Arg Ala Ser Met Pro Ala Pro Ala Thr Arg Gln Met Ile Arg Ala
            820             825             830

Ala Glu Glu Ser Ala Ser Gln Ile Gln Ser Ser Ala Gln Arg Leu Glu
        835             840             845

Thr Gln Val Ser Ala Ser Arg Ser Gln Met Glu Glu Asp Val Arg Arg
850             855             860
```

-continued

| | | | | | | | | | | | | | | |
|---|---|---|---|---|---|---|---|---|---|---|---|---|---|---|
| Thr 865 | Arg | Leu | Leu | Ile | Gln 870 | Gln | Val | Arg | Asp | Phe 875 | Leu | Thr | Asp | Pro | Asp 880 |
| Thr | Asp | Ala | Ala | Thr 885 | Ile | Gln | Glu | Val | Arg 890 | Arg | Ala | Val | Leu | Ala 895 | Leu |
| Trp | Leu | Pro | Thr 900 | Asp | Ser | Ala | Thr | Val 905 | Leu | Gln | Lys | Met 910 | Asn | Glu | Ile |
| Gln | Ala | Ile 915 | Ala | Ala | Arg | Leu | Pro 920 | Asn | Val | Asp | Leu | Val 925 | Leu | Ser | Gln |
| Thr | Lys 930 | Gln | Asp | Ile | Gly | Gly 935 | Ala | Arg | Arg | Leu | Gln 940 | Ala | Glu | Ala | Glu |
| Glu 945 | Ala | Arg | Ser | Arg | Ala 950 | His | Ala | Val | Glu | Gly 955 | Gln | Val | Glu | Asp | Val 960 |
| Val | Gly | Asn | Leu | Arg 965 | Gln | Gly | Thr | Val | Ala 970 | Leu | Gln | Glu | Ala | Gln 975 | Asp |
| Thr | Met | Gln | Gly 980 | Thr | Ser | Arg | Ser | Leu 985 | Arg | Leu | Ile | Gln 990 | Asp | Arg | Val |
| Ala | Glu | Val 995 | Gln | Gln | Val | Leu | Gly 1000 | Gln | Gln | Lys | Leu | Val 1005 | Thr | Ser | Met |
| Thr | Lys 1010 | Gln | Leu | Gly | Asp | Phe 1015 | Trp | Thr | Arg | Met | Glu 1020 | Glu | Leu | Arg | His |
| Gln 1025 | Ala | Arg | Gln | Gln | Gly 1030 | Ala | Glu | Ala | Val | Gln 1035 | Ala | Gln | Gln | Leu | Ala 1040 |
| Glu | Gly | Ala | Ser | Glu 1045 | Gln | Ala | Leu | Ser | Ala 1050 | Gln | Glu | Gly | Phe | Glu 1055 | Arg |
| Ile | Lys | Gln | Lys 1060 | Tyr | Ala | Glu | Leu | Lys 1065 | Asp | Arg | Leu | Gly | Gln 1070 | Ser | Ser |
| Met | Leu | Gly | Glu 1075 | Gln | Gly | Ala | Arg | Ile 1080 | Gln | Ser | Val | Lys | Thr 1085 | Glu | Ala |
| Glu | Glu | Leu 1090 | Phe | Gly | Glu | Thr | Met 1095 | Glu | Met | Asp | Arg | Met 1100 | Lys | Asp |
| Met | Glu | Leu 1105 | Glu | Leu | Leu | Arg 1110 | Ala | Ala | Gly | His | His 1115 | Ala | Ala | Leu | Ser 1120 |
| Asp | Leu | Thr | Gly | Leu 1125 | Glu | Lys | Arg | Val | Glu 1130 | Gln | Ile | Arg | Asp | His 1135 | Ile |
| Asn | Gly | Arg | Val 1140 | Leu | Tyr | Tyr | Ser | Thr 1145 | Cys | Lys | | | | | |

( 2 ) INFORMATION FOR SEQ ID NO:4:

( i ) SEQUENCE CHARACTERISTICS:
        ( A ) LENGTH: 1196 amino acids
        ( B ) TYPE: amino acid
        ( D ) TOPOLOGY: linear ( i i ) MOLECULE TYPE: peptide ( v ) FRAGMENT TYPE: internal ( i x ) FEATURE:
        ( A ) NAME/KEY: Domain
        ( B ) LOCATION: 1..250

( i x ) FEATURE:
        ( A ) NAME/KEY: Domain
        ( B ) LOCATION: 251..437

( i x ) FEATURE:
        ( A ) NAME/KEY: Domain
        ( B ) LOCATION: 438..807

( i x ) FEATURE:

(A) NAME/KEY: Domain
(B) LOCATION: 808..840

(ix) FEATURE:
(A) NAME/KEY: Domain
(B) LOCATION: 841..1196

(xi) SEQUENCE DESCRIPTION: SEQ ID NO:4:

```
Gln Glu Pro Glu Phe Ser Tyr Gly Cys Ala Glu Gly Ser Cys Tyr Pro
 1               5                  10                  15

Ala Thr Gly Asp Leu Leu Ile Gly Arg Ala Gln Lys Leu Ser Val Thr
            20                  25                  30

Ser Thr Thr Cys Gly Leu His Lys Pro Glu Pro Tyr Cys Ile Val Ser
        35                  40                  45

His Leu Gln Glu Asp Lys Lys Cys Phe Ile Cys Asn Ser Gln Asp Pro
    50                  55                  60

Tyr His Glu Thr Leu Asn Pro Asp Ser His Leu Ile Glu Asn Val Val
 65                  70                  75                  80

Thr Thr Phe Ala Pro Asn Arg Leu Lys Ile Trp Trp Gln Ser Glu Asn
                85                  90                  95

Gly Val Glu Asn Val Thr Ile Gln Leu Asp Leu Glu Ala Glu Phe His
                100                 105                 110

Phe Thr His Leu Ile Met Thr Phe Lys Thr Phe Arg Pro Ala Ala Met
            115                 120                 125

Leu Ile Glu Arg Ser Ser Asp Phe Gly Lys Thr Trp Gly Val Tyr Arg
    130                 135                 140

Tyr Phe Ala Tyr Asp Cys Glu Ala Ser Phe Pro Gly Ile Ser Thr Gly
145                 150                 155                 160

Pro Met Lys Lys Val Asp Asp Ile Ile Cys Asp Ser Arg Tyr Ser Asp
                165                 170                 175

Ile Glu Pro Ser Thr Glu Gly Glu Val Ile Phe Arg Ala Leu Asp Pro
            180                 185                 190

Ala Phe Lys Ile Glu Asp Pro Tyr Ser Pro Arg Ile Gln Asn Leu Leu
    195                 200                 205

Lys Ile Thr Asn Leu Arg Ile Lys Phe Val Lys Leu His Thr Leu Gly
    210                 215                 220

Asp Asn Leu Leu Asp Ser Arg Met Glu Ile Arg Glu Lys Tyr Tyr Tyr
225                 230                 235                 240

Ala Val Tyr Asp Met Val Val Arg Gly Asn Cys Phe Cys Tyr Gly His
                245                 250                 255

Ala Ser Glu Cys Ala Pro Val Asp Gly Phe Asn Glu Glu Val Glu Gly
            260                 265                 270

Met Val His Gly His Cys Met Cys Arg His Asn Thr Lys Gly Leu Asn
            275                 280                 285

Cys Glu Leu Cys Met Asp Phe Tyr His Asp Leu Pro Trp Arg Pro Ala
    290                 295                 300

Glu Gly Arg Asn Ser Asn Ala Cys Lys Lys Cys Asn Cys Asn Glu His
305                 310                 315                 320

Ser Ile Ser Cys His Phe Asp Met Ala Val Tyr Leu Ala Thr Gly Asn
                325                 330                 335

Val Ser Gly Gly Val Cys Asp Asp Cys Gln His Asn Thr Met Gly Arg
            340                 345                 350

Asn Cys Glu Gln Cys Lys Pro Phe Tyr Tyr Gln His Pro Glu Arg Asp
    355                 360                 365

Ile Arg Asp Pro Asn Phe Cys Glu Arg Cys Thr Cys Asp Pro Ala Gly
    370                 375                 380
```

| | | | | | | | | | | | | | | |
|---|---|---|---|---|---|---|---|---|---|---|---|---|---|---|
| Ser 385 | Gln | Asn | Glu | Gly 390 | Ile | Cys | Asp | Ser | Tyr 395 | Thr | Asp | Phe | Ser | Thr Gly 400 |
| Leu | Ile | Ala | Gly | Gln 405 | Cys | Arg | Cys | Lys | Leu 410 | Asn | Val | Glu | Gly | Glu His 415 |
| Cys | Asp | Val | Cys 420 | Lys | Glu | Gly | Phe | Tyr 425 | Asp | Leu | Ser | Ser 430 | Glu | Pro |
| Phe | Gly | Cys 435 | Lys | Ser | Cys | Val | Cys 440 | Asn | Tyr | Leu | Gly | Thr 445 | Val | Gln Glu |
| His | Cys 450 | Asn | Gly | Ser | Asp | Cys 455 | Gln | Cys | Asp | Lys | Ala 460 | Thr | Gly | Gln Cys |
| Leu 465 | Cys | Leu | Pro | Asn | Val 470 | Ile | Gly | Gln | Asn | Cys 475 | Asp | Arg | Cys | Ala Pro 480 |
| Asn | Thr | Trp | Gln | Leu 485 | Ala | Ser | Gly | Thr | Gly 490 | Cys | Asp | Pro | Cys | Asn Cys 495 |
| Asn | Ala | Ala | His 500 | Ser | Phe | Gly | Pro | Ser 505 | Cys | Asn | Glu | Phe | Thr 510 | Gly Gln |
| Cys | Gln | Cys 515 | Met | Pro | Gly | Phe | Gly 520 | Gly | Arg | Thr | Cys | Ser 525 | Glu | Cys Gln |
| Glu | Leu 530 | Phe | Trp | Gly | Asp | Pro 535 | Val | Glu | Cys | Arg | Ala 540 | Cys | Asp | Cys |
| Asp 545 | Pro | Arg | Gly | Ile | Glu 550 | Thr | Pro | Gln | Cys | Asp 555 | Gln | Ser | Thr | Gly Gln 560 |
| Cys | Val | Cys | Val | Glu 565 | Gly | Val | Glu | Gly | Pro 570 | Arg | Cys | Asp | Lys | Cys Thr 575 |
| Arg | Gly | Tyr | Ser 580 | Gly | Val | Phe | Pro | Asp 585 | Cys | Thr | Pro | Cys 590 | His | Gln Cys |
| Phe | Ala | Leu 595 | Trp | Asp | Val | Ile | Ile 600 | Ala | Glu | Leu | Thr | Asn 605 | Arg | Thr His |
| Arg | Phe 610 | Leu | Glu | Lys | Ala | Lys 615 | Ala | Leu | Lys | Ile | Ser 620 | Gly | Val | Ile Gly |
| Pro 625 | Tyr | Arg | Glu | Thr | Val 630 | Asp | Ser | Val | Glu | Arg 635 | Lys | Val | Ser | Glu Ile 640 |
| Lys | Asp | Ile | Leu | Ala 645 | Gln | Ser | Pro | Ala | Ala 650 | Glu | Pro | Leu | Lys | Asn Ile 655 |
| Gly | Asn | Leu | Phe 660 | Glu | Glu | Ala | Glu | Lys 665 | Leu | Ile | Lys | Asp | Val 670 | Thr Glu |
| Met | Met | Ala 675 | Gln | Val | Glu | Val | Lys 680 | Leu | Ser | Asp | Thr | Thr 685 | Ser | Gln Ser |
| Asn | Ser 690 | Thr | Ala | Lys | Glu | Leu 695 | Asp | Ser | Leu | Gln | Thr 700 | Glu | Ala | Glu Ser |
| Leu 705 | Asp | Asn | Thr | Val | Lys 710 | Glu | Leu | Ala | Glu | Gln 715 | Leu | Glu | Phe | Ile Lys 720 |
| Asn | Ser | Asp | Ile | Arg 725 | Gly | Ala | Leu | Asp | Ser 730 | Ile | Thr | Lys | Tyr | Phe Gln 735 |
| Met | Ser | Leu | Glu 740 | Ala | Glu | Glu | Arg | Val 745 | Asn | Ala | Ser | Thr | Thr 750 | Glu Pro |
| Asn | Ser | Thr 755 | Val | Glu | Gln | Ser | Ala 760 | Leu | Met | Arg | Asp | Arg 765 | Val | Glu Asp |
| Val | Met 770 | Met | Glu | Arg | Glu | Ser 775 | Gln | Phe | Lys | Glu | Lys 780 | Gln | Glu | Glu Gln |
| Ala 785 | Arg | Leu | Leu | Asp | Glu 790 | Leu | Ala | Gly | Lys | Leu 795 | Gln | Ser | Leu | Asp Leu 800 |
| Ser | Ala | Ala | Ala | Glu | Met | Thr | Cys | Gly | Thr | Pro | Pro | Gly | Ala | Ser Cys |

|       |       |       |       | 805   |       |       |       | 810   |       |       |       |       | 815   |       |
|-------|-------|-------|-------|-------|-------|-------|-------|-------|-------|-------|-------|-------|-------|-------|

Ser Glu Thr Glu Cys Gly Gly Pro Asn Cys Arg Thr Asp Glu Gly Glu
              820                 825                 830

Arg Lys Cys Gly Gly Pro Gly Cys Gly Gly Leu Val Thr Val Ala His
          835                 840                 845

Asn Ala Trp Gln Lys Ala Met Asp Leu Asp Gln Asp Val Leu Ser Ala
      850                 855                 860

Leu Ala Glu Val Glu Gln Leu Ser Lys Met Val Ser Glu Ala Lys Leu
865                 870                 875                 880

Arg Ala Asp Glu Ala Lys Gln Ser Ala Glu Asp Ile Leu Leu Lys Thr
                  885                 890                 895

Asn Ala Thr Lys Glu Lys Met Asp Lys Ser Asn Glu Glu Leu Arg Asn
              900                 905                 910

Leu Ile Lys Gln Ile Arg Asn Phe Leu Thr Gln Asp Ser Ala Asp Leu
          915                 920                 925

Asp Ser Ile Glu Ala Val Ala Asn Glu Val Leu Lys Met Glu Met Pro
      930                 935                 940

Ser Thr Pro Gln Gln Leu Gln Asn Leu Thr Glu Asp Ile Arg Glu Arg
945                 950                 955                 960

Val Glu Ser Leu Ser Gln Val Glu Val Ile Leu Gln His Ser Ala Ala
                  965                 970                 975

Asp Ile Ala Arg Ala Glu Met Leu Leu Glu Glu Ala Lys Arg Ala Ser
              980                 985                 990

Lys Ser Ala Thr Asp Val Lys Val Thr Ala Asp Met Val Lys Glu Ala
          995                 1000                1005

Leu Glu Glu Ala Glu Lys Ala Gln Val Ala Ala Glu Lys Ala Ile Lys
      1010                1015                1020

Gln Ala Asp Glu Asp Ile Gln Gly Thr Gln Asn Leu Leu Thr Ser Ile
1025                1030                1035                1040

Glu Ser Glu Thr Ala Ala Ser Glu Glu Thr Leu Phe Asn Ala Ser Gln
                  1045                1050                1055

Arg Ile Ser Glu Leu Glu Arg Asn Val Glu Glu Leu Lys Arg Lys Ala
              1060                1065                1070

Ala Gln Asn Ser Gly Glu Ala Glu Tyr Ile Glu Lys Val Val Tyr Thr
          1075                1080                1085

Val Lys Gln Ser Ala Glu Asp Val Lys Lys Thr Leu Asp Gly Glu Leu
      1090                1095                1100

Asp Glu Lys Tyr Lys Lys Val Glu Asn Leu Ile Ala Lys Lys Thr Glu
1105                1110                1115                1120

Glu Ser Ala Asp Ala Arg Arg Lys Ala Glu Met Leu Gln Asn Glu Ala
                  1125                1130                1135

Lys Thr Leu Leu Ala Gln Ala Asn Ser Lys Leu Gln Leu Leu Lys Asp
              1140                1145                1150

Leu Glu Arg Lys Tyr Glu Asp Asn Gln Arg Tyr Leu Glu Asp Lys Ala
          1155                1160                1165

Gln Glu Leu Ala Arg Leu Glu Gly Glu Val Arg Ser Leu Leu Lys Asp
      1170                1175                1180

Ile Ser Gln Lys Val Ala Val Tyr Ser Thr Cys Leu
1185                1190                1195

( 2 ) INFORMATION FOR SEQ ID NO:5:

( i ) SEQUENCE CHARACTERISTICS:
        ( A ) LENGTH: 231 amino acids
        ( B ) TYPE: amino acid (D) TOPOLOGY: linear (ii) MOLECULE TYPE: peptide (v) FRAGMENT TYPE: internal (xi) SEQUENCE DESCRIPTION: SEQ ID NO:5:

| Gln | Gln | Ala | Cys | Ser | Arg | Gly | Ala | Cys | Tyr | Pro | Pro | Val | Gly | Asp | Leu |
|---|---|---|---|---|---|---|---|---|---|---|---|---|---|---|---|
| 1 | | | | 5 | | | | | 10 | | | | | 15 | |
| Leu | Val | Gly | Arg | Thr | Arg | Phe | Leu | Arg | Ala | Ser | Ser | Thr | Cys | Gly | Leu |
| | | | 20 | | | | 25 | | | | | 30 | | | |
| Thr | Lys | Pro | Glu | Thr | Tyr | Cys | Thr | Gln | Tyr | Gly | Glu | Trp | Gln | Met | Lys |
| | | 35 | | | | | 40 | | | | | 45 | | | |
| Cys | Cys | Lys | Cys | Asn | Ser | Arg | Gln | Pro | His | Asn | Tyr | Tyr | Ser | His | Arg |
| | 50 | | | | | 55 | | | | | | 60 | | | |
| Val | Glu | Asn | Val | Ala | Ser | Ser | Ser | Gly | Pro | Met | Arg | Trp | Trp | Gln | Ser |
| 65 | | | | | 70 | | | | | 75 | | | | | 80 |
| Gln | Asn | Asp | Val | Asn | Pro | Val | Ser | Leu | Gln | Leu | Asp | Leu | Asp | Arg | Arg |
| | | | | 85 | | | | | 90 | | | | | 95 | |
| Phe | Gln | Leu | Gln | Glu | Val | Met | Met | Glu | Phe | Pro | Gly | Ala | His | Ala | Ala |
| | | | 100 | | | | | 105 | | | | | 110 | | |
| Gly | Met | Leu | Ile | Glu | Arg | Ser | Ser | Asp | Phe | Gly | Lys | Thr | Trp | Arg | Val |
| | | | 115 | | | | | 120 | | | | | 125 | | |
| Tyr | Gln | Tyr | Leu | Ala | Ala | Asp | Cys | Thr | Ser | Thr | Phe | Pro | Arg | Val | Arg |
| | | 130 | | | | | 135 | | | | | 140 | | | |
| Gln | Gly | Arg | Pro | Gln | Ser | Trp | Gln | Asp | Val | Arg | Cys | Gln | Ser | Leu | Pro |
| 145 | | | | | 150 | | | | | 155 | | | | | 160 |
| Gln | Arg | Pro | Asn | Ala | Arg | Leu | Asn | Gly | Gly | Lys | Val | Gln | Leu | Asn | Leu |
| | | | | 165 | | | | | 170 | | | | | 175 | |
| Met | Asp | Leu | Val | Ser | Gly | Ile | Glu | Ala | Thr | Gln | Ser | Gln | Lys | Ile | Gln |
| | | | 180 | | | | | 185 | | | | | 190 | | |
| Glu | Val | Gly | Glu | Ile | Thr | Asn | Leu | Arg | Ile | Lys | Phe | Val | Lys | Leu | Ala |
| | | | 195 | | | | 200 | | | | | 205 | | | |
| Pro | Val | Pro | Lys | Leu | Asp | His | Pro | Pro | Ser | Ala | Tyr | Tyr | Ala | Val | Ser |
| | 210 | | | | | 215 | | | | | 220 | | | | |
| Gln | Leu | Arg | Leu | Gln | Gly | Ser | | | | | | | | | |
| 225 | | | | | 230 | | | | | | | | | | |

(2) INFORMATION FOR SEQ ID NO:6:

(i) SEQUENCE CHARACTERISTICS:
  (A) LENGTH: 249 amino acids
  (B) TYPE: amino acid
  (D) TOPOLOGY: linear (ii) MOLECULE TYPE: peptide (v) FRAGMENT TYPE: internal (xi) SEQUENCE DESCRIPTION: SEQ ID NO:6:

| Gln | Glu | Pro | Glu | Phe | Ser | Tyr | Gly | Cys | Ala | Glu | Gly | Ser | Cys | Tyr | Pro |
|---|---|---|---|---|---|---|---|---|---|---|---|---|---|---|---|
| 1 | | | | 5 | | | | | 10 | | | | | 15 | |
| Ala | Thr | Gly | Asp | Leu | Leu | Ile | Gly | Arg | Ala | Gln | Lys | Leu | Ser | Val | Thr |
| | | | 20 | | | | 25 | | | | | 30 | | | |
| Ser | Thr | Cys | Gly | Leu | His | Lys | Pro | Glu | Pro | Tyr | Cys | Ile | Val | Ser | His |
| | | | 35 | | | | 40 | | | | | 45 | | | |
| Leu | Gln | Glu | Asp | Lys | Lys | Cys | Phe | Ile | Cys | Asn | Ser | Gln | Asp | Pro | Tyr |
| | | 50 | | | | | 55 | | | | | 60 | | | |
| His | Glu | Thr | Leu | Asn | Pro | Asp | Ser | His | Leu | Ile | Glu | Asn | Val | Val | Thr |

|  |  |  |  | 65 |  |  |  | 70 |  |  |  | 75 |  |  |  | 80 |
|---|---|---|---|---|---|---|---|---|---|---|---|---|---|---|---|---|
| Thr | Phe | Ala | Pro | Asn | Arg | Leu | Lys | Ile | Trp | Trp | Gln | Ser | Glu | Asn | Gly |
|  |  |  |  | 85 |  |  |  |  | 90 |  |  |  |  | 95 |  |
| Val | Glu | Asn | Val | Thr | Ile | Gln | Leu | Asp | Leu | Glu | Ala | Glu | Phe | His | Phe |
|  |  |  | 100 |  |  |  |  | 105 |  |  |  |  | 110 |  |  |
| Thr | His | Leu | Ile | Met | Thr | Phe | Lys | Thr | Phe | Arg | Pro | Ala | Ala | Met | Leu |
|  |  |  | 115 |  |  |  |  | 120 |  |  |  |  | 125 |  |  |
| Ile | Glu | Arg | Ser | Ser | Asp | Phe | Gly | Lys | Thr | Trp | Gly | Val | Tyr | Arg | Tyr |
|  |  | 130 |  |  |  |  | 135 |  |  |  |  | 140 |  |  |  |
| Phe | Ala | Tyr | Asp | Cys | Glu | Ala | Ser | Phe | Pro | Gly | Ile | Ser | Thr | Gly | Pro |
| 145 |  |  |  |  | 150 |  |  |  |  | 155 |  |  |  |  | 160 |
| Met | Lys | Lys | Val | Asp | Asp | Ile | Ile | Cys | Asp | Ser | Arg | Tyr | Ser | Asp | Ile |
|  |  |  |  | 165 |  |  |  |  | 170 |  |  |  |  | 175 |  |
| Glu | Pro | Ser | Thr | Glu | Gly | Glu | Val | Ile | Phe | Arg | Ala | Leu | Asp | Pro | Ala |
|  |  |  | 180 |  |  |  |  | 185 |  |  |  |  | 190 |  |  |
| Phe | Lys | Ile | Glu | Asp | Pro | Tyr | Ser | Pro | Arg | Ile | Gln | Asn | Leu | Leu | Lys |
|  |  | 195 |  |  |  |  | 200 |  |  |  |  | 205 |  |  |  |
| Ile | Thr | Asn | Leu | Arg | Ile | Lys | Phe | Val | Lys | Leu | His | Thr | Leu | Gly | Asp |
|  | 210 |  |  |  |  | 215 |  |  |  |  | 220 |  |  |  |  |
| Asn | Leu | Leu | Asp | Ser | Arg | Met | Glu | Ile | Arg | Glu | Lys | Tyr | Tyr | Tyr | Ala |
| 225 |  |  |  |  | 230 |  |  |  |  | 235 |  |  |  |  | 240 |
| Val | Tyr | Asp | Met | Val | Val | Arg | Gly | Asn |  |  |  |  |  |  |  |
|  |  |  |  | 245 |  |  |  |  |  |  |  |  |  |  |  |

( 2 ) INFORMATION FOR SEQ ID NO:7:

( i ) SEQUENCE CHARACTERISTICS:
  ( A ) LENGTH: 250 amino acids
  ( B ) TYPE: amino acid
  ( D ) TOPOLOGY: linear ( i i ) MOLECULE TYPE: peptide ( v ) FRAGMENT TYPE: internal ( x i ) SEQUENCE DESCRIPTION: SEQ ID NO:7:

| Gln | Val | Pro | Ser | Leu | Asp | Val | Pro | Gly | Cys | Ser | Arg | Gly | Ser | Cys | Tyr |
|---|---|---|---|---|---|---|---|---|---|---|---|---|---|---|---|
| 1 |  |  |  | 5 |  |  |  |  | 10 |  |  |  |  | 15 |  |
| Pro | Ala | Thr | Gly | Asp | Leu | Leu | Val | Gly | Arg | Ala | Asp | Arg | Leu | Thr | Ala |
|  |  |  | 20 |  |  |  |  | 25 |  |  |  |  | 30 |  |  |
| Ser | Ser | Thr | Cys | Gly | Leu | His | Ser | Pro | Gln | Pro | Tyr | Cys | Ile | Val | Ser |
|  |  | 35 |  |  |  |  | 40 |  |  |  |  | 45 |  |  |  |
| His | Leu | Gln | Asp | Glu | Lys | Lys | Cys | Phe | Leu | Cys | Asp | Ser | Arg | Arg | Pro |
|  | 50 |  |  |  |  | 55 |  |  |  |  | 60 |  |  |  |  |
| Phe | Ser | Ala | Arg | Asp | Asn | Pro | Asn | Ser | His | Arg | Ile | Gln | Asn | Val | Val |
| 65 |  |  |  | 70 |  |  |  |  | 75 |  |  |  |  |  | 80 |
| Thr | Ser | Phe | Ala | Pro | Gln | Arg | Arg | Thr | Ala | Trp | Trp | Gln | Ser | Glu | Asn |
|  |  |  |  | 85 |  |  |  |  | 90 |  |  |  |  | 95 |  |
| Gly | Val | Pro | Met | Val | Thr | Ile | Gln | Leu | Asp | Leu | Glu | Ala | Glu | Phe | His |
|  |  |  | 100 |  |  |  |  | 105 |  |  |  |  | 110 |  |  |
| Phe | Thr | His | Leu | Ile | Met | Thr | Phe | Lys | Thr | Phe | Arg | Pro | Ala | Ala | Met |
|  |  | 115 |  |  |  |  | 120 |  |  |  |  | 125 |  |  |  |
| Leu | Val | Glu | Arg | Ser | Ala | Asp | Phe | Gly | Arg | Thr | Trp | Arg | Val | Tyr | Arg |
|  | 130 |  |  |  |  | 135 |  |  |  |  | 140 |  |  |  |  |
| Tyr | Phe | Ser | Tyr | Asp | Cys | Gly | Ala | Asp | Phe | Pro | Gly | Ile | Pro | Leu | Ala |
| 145 |  |  |  |  | 150 |  |  |  |  | 155 |  |  |  |  | 160 |
| Pro | Pro | Arg | Arg | Trp | Asp | Asp | Val | Val | Cys | Glu | Ser | Arg | Tyr | Ser | Glu |

|       |       |       |       | 165   |       |       |       | 170   |       |       |       | 175   |       |       |
|-------|-------|-------|-------|-------|-------|-------|-------|-------|-------|-------|-------|-------|-------|-------|
| Ile   | Glu   | Pro   | Ser   | Thr   | Glu   | Gly   | Glu   | Val   | Ile   | Tyr   | Arg   | Val   | Leu   | Asp Pro |
|       |       |       | 180   |       |       |       |       | 185   |       |       |       | 190   |       |       |
| Ala   | Ile   | Pro   | Ile   | Pro   | Asp   | Pro   | Tyr   | Ser   | Ser   | Arg   | Ile   | Gln   | Asn   | Leu Leu |
|       |       |       | 195   |       |       |       |       | 200   |       |       |       | 205   |       |       |
| Lys   | Ile   | Thr   | Asn   | Leu   | Arg   | Val   | Asn   | Leu   | Thr   | Arg   | Leu   | His   | Thr   | Leu Gly |
|       | 210   |       |       |       |       | 215   |       |       |       |       | 220   |       |       |       |
| Asp   | Asn   | Leu   | Leu   | Asp   | Pro   | Arg   | Arg   | Glu   | Ile   | Arg   | Glu   | Lys   | Tyr   | Tyr Tyr |
| 225   |       |       |       |       | 230   |       |       |       |       | 235   |       |       |       | 240   |
| Ala   | Leu   | Tyr   | Glu   | Leu   | Val   | Ile   | Arg   | Gly   | Asn   |       |       |       |       |       |
|       |       |       |       | 245   |       |       |       |       | 250   |       |       |       |       |       |

( 2 ) INFORMATION FOR SEQ ID NO:8:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:8:

| Glu | Ala | Leu | Lys | Leu | Lys | Arg | Ala | Gly | Asn | Ser | Leu | Ala | Ala | Ser Thr |
|-----|-----|-----|-----|-----|-----|-----|-----|-----|-----|-----|-----|-----|-----|---------|
| 1   |     |     |     | 5   |     |     |     |     | 10  |     |     |     |     | 15      |
| Ala | Glu | Glu | Thr | Ala | Gly | Ser | Ala | Gln | Ser | Arg | Ala | Arg | Glu | Ala Glu |
|     |     |     | 20  |     |     |     |     | 25  |     |     |     | 30  |     |         |
| Lys | Gln | Leu | Arg | Glu | Gln | Val | Gly |     |     |     |     |     |     |         |
|     |     |     | 35  |     |     |     | 40  |     |     |     |     |     |     |         |

( 2 ) INFORMATION FOR SEQ ID NO:9:

( i ) SEQUENCE CHARACTERISTICS:
        ( A ) LENGTH: 24 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:9:

| Ala | Gly | Asn | Ser | Leu | Ala | Ala | Ser | Thr | Ala | Glu | Glu | Thr | Ala | Gly Ser |
|-----|-----|-----|-----|-----|-----|-----|-----|-----|-----|-----|-----|-----|-----|---------|
| 1   |     |     |     | 5   |     |     |     |     | 10  |     |     |     |     | 15      |
| Ala | Gln | Gly | Arg | Ala | Gln | Glu | Ala |     |     |     |     |     |     |         |
|     |     |     | 20  |     |     |     |     |     |     |     |     |     |     |         |

( 2 ) INFORMATION FOR SEQ ID NO:10:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:10:

| Glu | Glu | Leu | Arg | His | Gln | Ala | Arg | Gln | Gln | Gly | Ala | Glu | Ala | Val Gln |
|-----|-----|-----|-----|-----|-----|-----|-----|-----|-----|-----|-----|-----|-----|---------|
| 1   |     |     |     | 5   |     |     |     |     | 10  |     |     |     |     | 15      |
| Ala | Gln | Gln | Leu | Ala | Glu | Gly | Ala | Ser | Glu | Gln | Ala | Leu | Ser | Ala Gln |
|     |     |     | 20  |     |     |     |     | 25  |     |     |     | 30  |     |         |

```
        Glu  Gly  Phe  Glu  Arg  Ile  Lys  Gln
                  35                       40
```

( 2 ) INFORMATION FOR SEQ ID NO:11:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:11:

```
Thr  Gly  Asp  Cys  Tyr  Ser  Gly  Asp  Glu  Asn  Pro  Asp  Ile  Glu  Cys  Ala
1                   5                        10                       15

Asp  Cys  Pro  Ile  Gly  Phe  Tyr  Asn  Asp  Pro  His  Asp  Pro  Arg  Ser  Cys
               20                       25                       30

Lys  Pro  Cys  Pro  Cys  His  Asn  Gly
               35                  40
```

( 2 ) INFORMATION FOR SEQ ID NO:12:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:12:

```
Asp  Glu  Asn  Pro  Asp  Ile  Glu  Cys  Ala  Asp  Cys  Pro  Ile  Gly  Phe  Tyr
1                   5                        10                       15

Asn
```

( 2 ) INFORMATION FOR SEQ ID NO:13:

( i ) SEQUENCE CHARACTERISTICS:
        ( A ) LENGTH: 40 amino acids
        ( B ) TYPE: amino acid
        ( D ) TOPOLOGY: linear ( i i ) MOLECULE TYPE: peptide ( v ) FRAGMENT TYPE: internal ( x i ) SEQUENCE DESCRIPTION: SEQ ID NO:13:

```
Lys  Val  Asp  Thr  Arg  Ala  Lys  Asn  Ala  Gly  Val  Thr  Ile  Gln  Asp  Thr
1                   5                        10                       15

Leu  Asn  Thr  Leu  Asp  Gly  Leu  Leu  His  Leu  Met  Asp  Gln  Pro  Leu  Ser
               20                       25                       30

Val  Asp  Glu  Glu  Gly  Leu  Val  Leu
               35                  40
```

( 2 ) INFORMATION FOR SEQ ID NO:14:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( v ) FRAGMENT TYPE: internal (xi) SEQUENCE DESCRIPTION: SEQ ID NO:14:

| Asn | Ala | Gly | Val | Thr | Ile | Gln | Asp | Thr | Leu | Asn | Thr | Leu | Asp | Gly | Leu |
|1| | | |5| | | |10| | | | |15| | |

| Leu | His | Leu | Met | Asp | Gln | Pro | Leu | Ser |
| | | |20| | | | |25|

What is claimed is:

1. A purified DNA which encodes a fragment of the B1k chain of laminin of SEQ ID NO:2 said fragment including all or part of domain VI and said fragment being at least 30 amino acid residues in length, provided that said fragment in not part of a full length B1k sequence and said fragment has the ability to bind to a K-laminin A chain.

2. A vector comprising the purified DNA sequence of claim 1, provided that said fragment in not part of a full length B1k sequence.

3. A cell containing the purified DNA of claim 2.

4. A method for manufacture of a fragment of the B1k chain of laminin of SEQ ID NO:2 said fragment including all or part of domain VI and said fragment being at least 30 amino acid residues in length, provided that said fragment in not part of a full length B1k sequence and said fragment has the ability to bind to a K-laminin A chain, comprising culturing the cell of claim 3 in a medium to express said B1k.

5. A cell containing the purified DNA of claim 1.

6. A method for manufacture of a a fragment of the B1k chain of laminin of SEQ ID NO:2 said fragment including all or part of domain VI and said fragment being at least 30 amino acid residues in length, provided that said fragment in not part of a full length B1k sequence and said fragment has the ability to bind to a K-laminin A chain, comprising culturing the cell of claim 5 in a medium to express said B1k fragment.

7. The purified DNA of claim 1, wherein said fragment is at least 60 amino acid residues in length.

8. The purified DNA of claim 1, wherein said fragment is at least 100 amino acid residues in length.

9. The purified DNA of claim 1, wherein said fragment is at least 200 amino acid residues in length.

* * * * *